(12) United States Patent
Fischl et al.

(10) Patent No.: US 12,214,351 B2
(45) Date of Patent: Feb. 4, 2025

(54) DEVELOPER SOLUTION VIAL

(71) Applicant: ORASURE TECHNOLOGIES, INC., Bethlehem, PA (US)

(72) Inventors: Mark Fischl, Bethlehem, PA (US); Keith Kardos, Bethlehem, PA (US); Attila Nemeth, Bethlehem, PA (US); Mark Emrick, Bethlehem, PA (US)

(73) Assignee: OraSure Technologies, Inc., Bethlehem, PA (US)

( * ) Notice: Subject to any disclaimer, the term of this patent is extended or adjusted under 35 U.S.C. 154(b) by 0 days.

(21) Appl. No.: 17/546,440

(22) Filed: Dec. 9, 2021

(65) Prior Publication Data

US 2022/0184606 A1    Jun. 16, 2022

Related U.S. Application Data

(60) Provisional application No. 63/124,315, filed on Dec. 11, 2020.

(51) Int. Cl.
*B01L 3/00* (2006.01)
*G01N 33/543* (2006.01)

(52) U.S. Cl.
CPC ...... *B01L 3/5029* (2013.01); *G01N 33/54388* (2021.08); *B01L 2200/16* (2013.01); *B01L 2300/069* (2013.01); *B01L 2300/0832* (2013.01)

(58) Field of Classification Search
CPC ............... B01L 3/5029; B01L 2200/16; B01L 2300/069; B01L 2300/0832; B01L 2200/026; B01L 3/5082; G01N 33/54388
See application file for complete search history.

(56) References Cited

U.S. PATENT DOCUMENTS

| | | |
|---|---|---|
| 2006/0057027 A1 | 3/2006 | Hudak et al. |
| 2009/0024060 A1* | 1/2009 | Darrigrand ........ A61B 10/0051 600/584 |
| 2020/0155127 A1 | 5/2020 | Fry et al. |
| 2020/0371100 A1 | 11/2020 | Yearwood |

FOREIGN PATENT DOCUMENTS

WO    WO-2019032669 A1 *    2/2019    ......... C07K 16/1045

* cited by examiner

*Primary Examiner* — Dennis White
(74) *Attorney, Agent, or Firm* — RAPHAEL BELLUM PLLC

(57) ABSTRACT

The invention provides a developer solution vial and methods of its use to diagnose diseases using a sampling and/or assay device, for example, for use with a lateral flow assay (LFA) device. The developer solution vial may include any container that is capable of holding developer solution. The developer solution vial is keyed to the sampling and/or assay device. The developer solution vial minimizes the amount of developer solution required for accurate fluid flow assay testing.

19 Claims, 32 Drawing Sheets

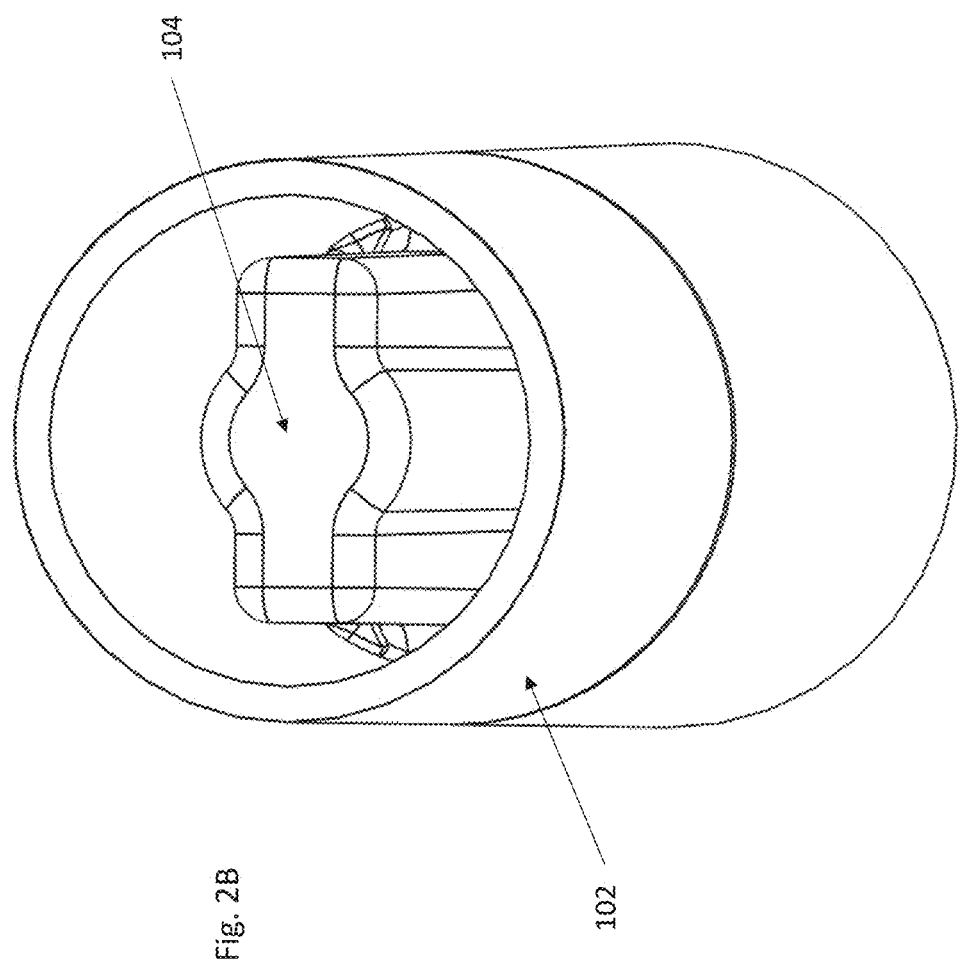

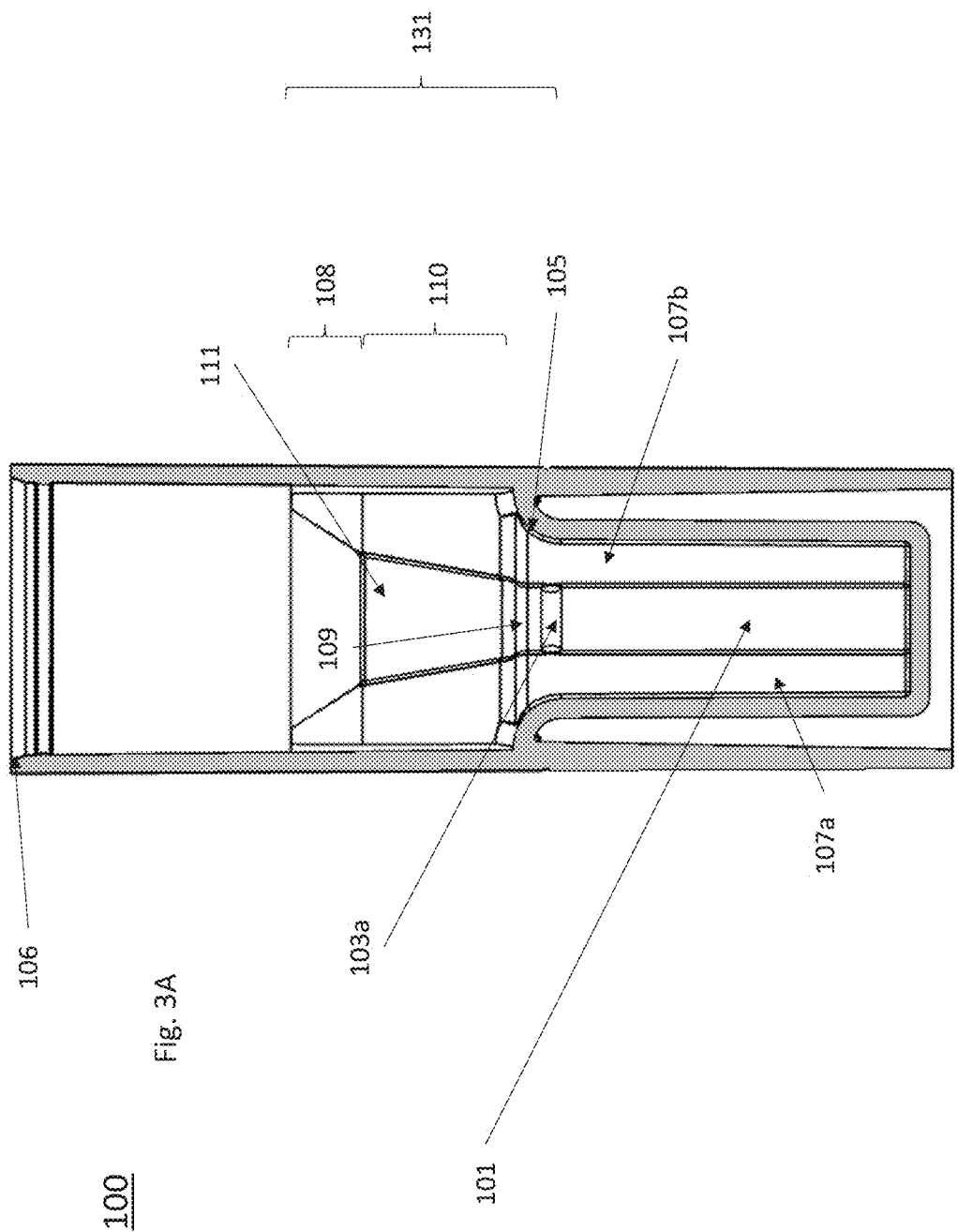

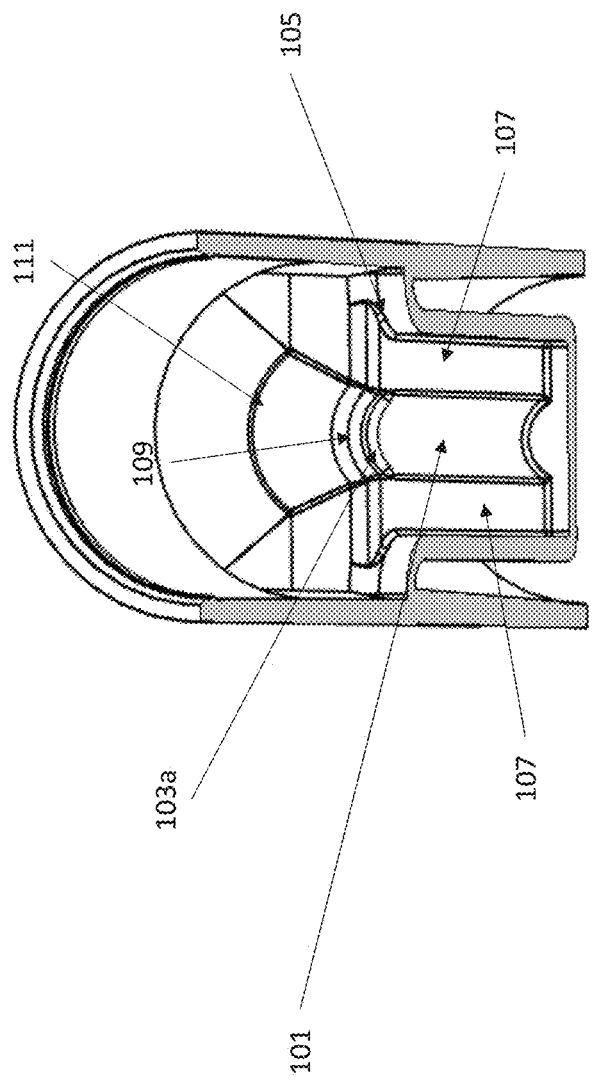

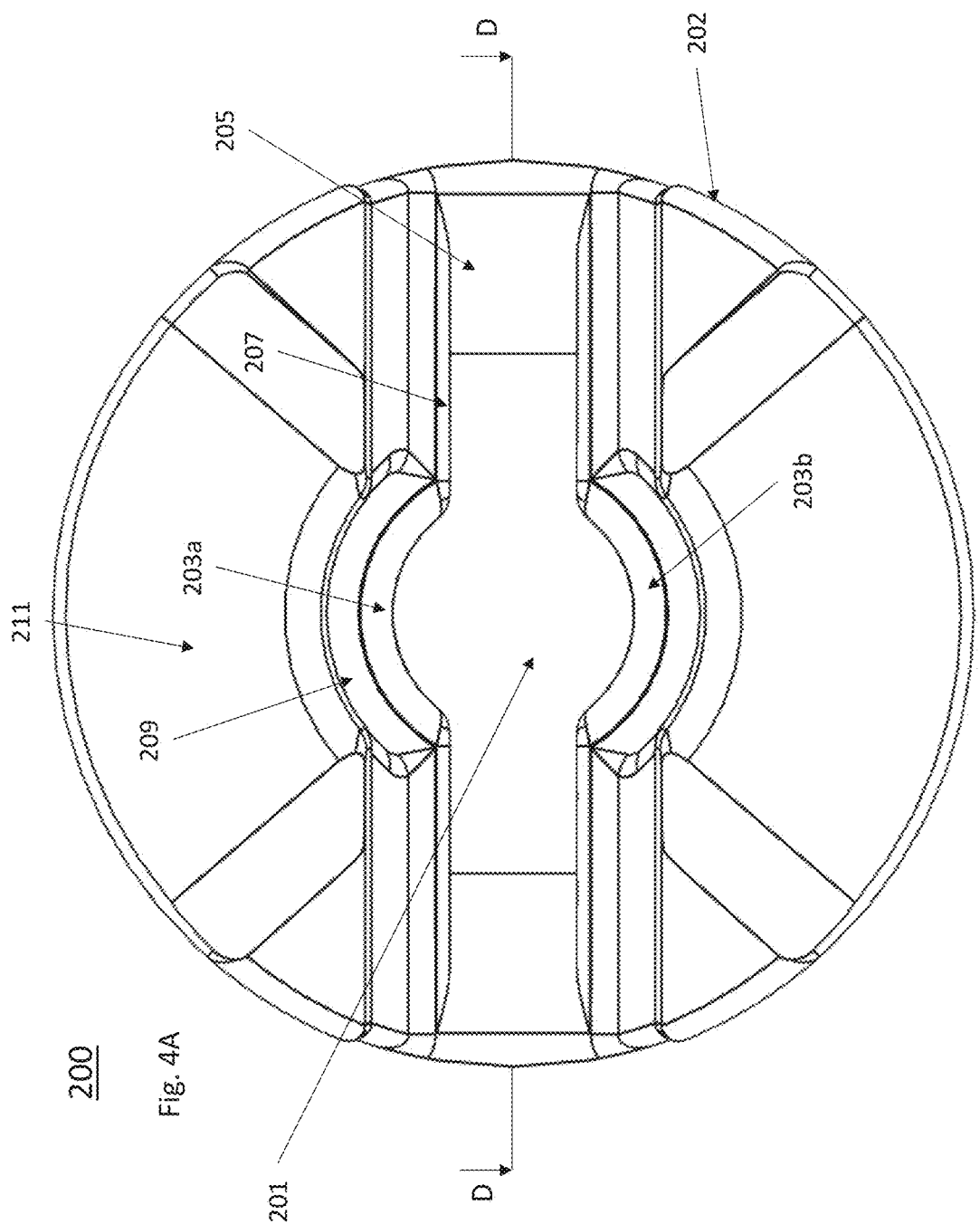

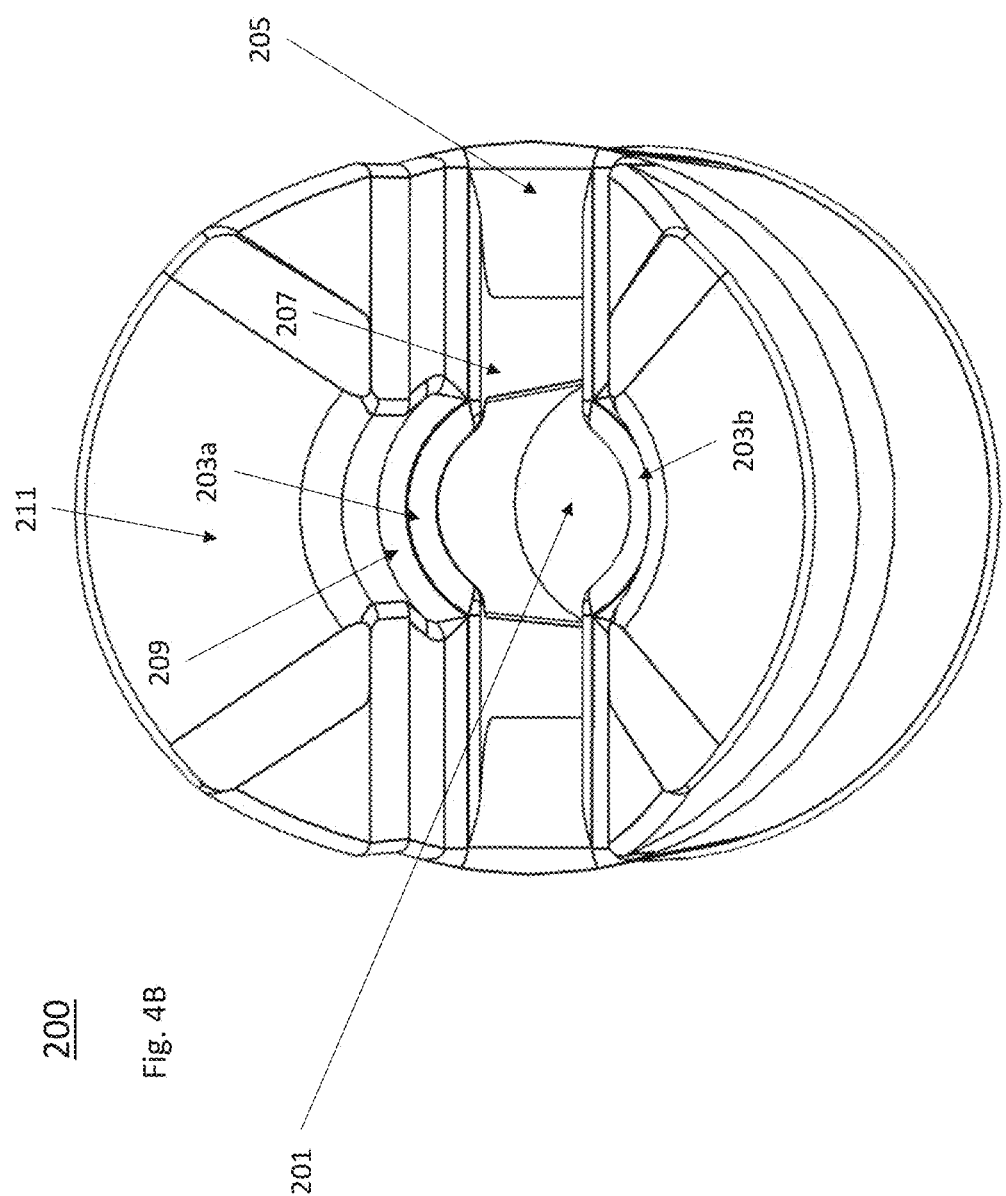

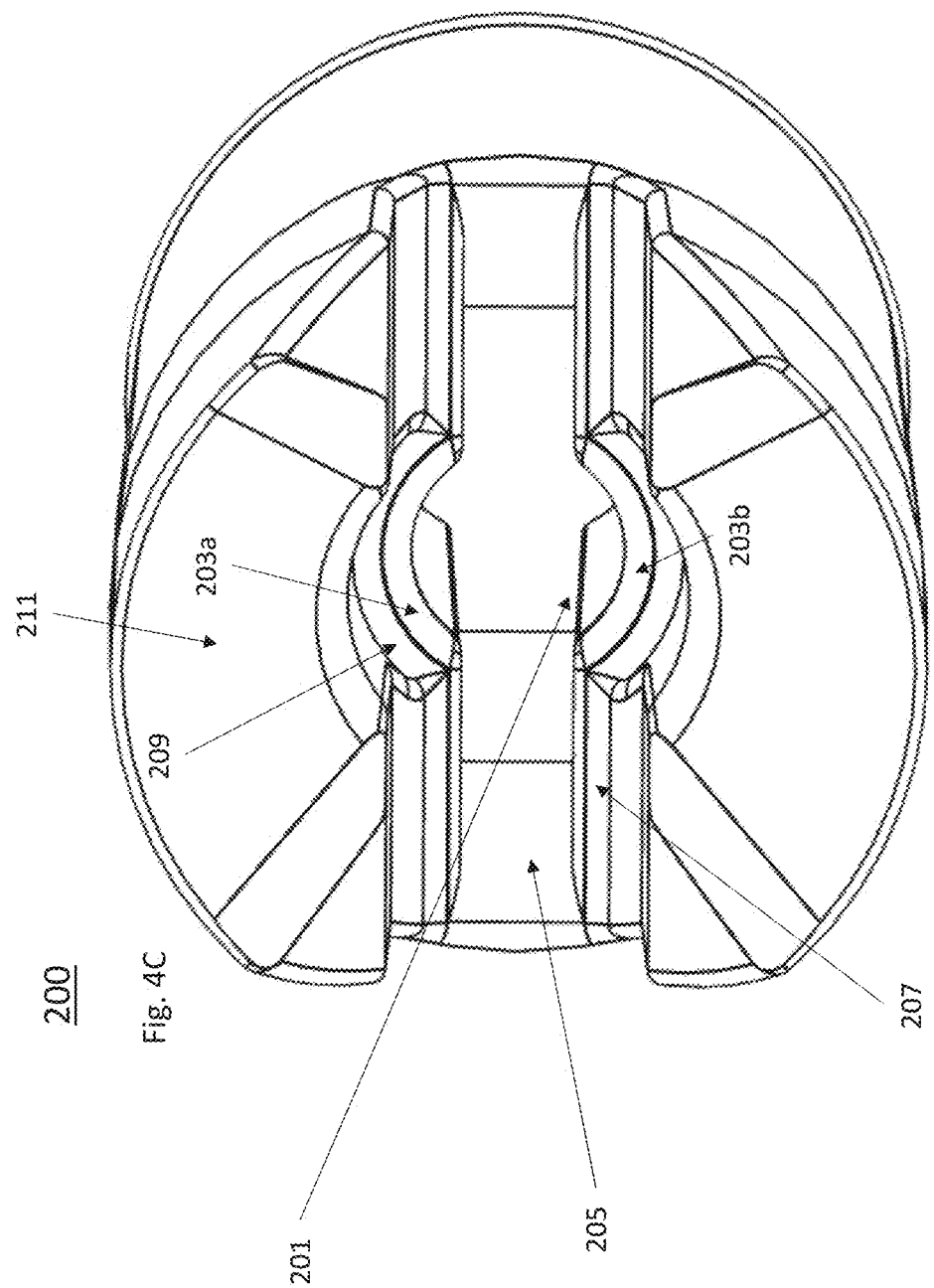

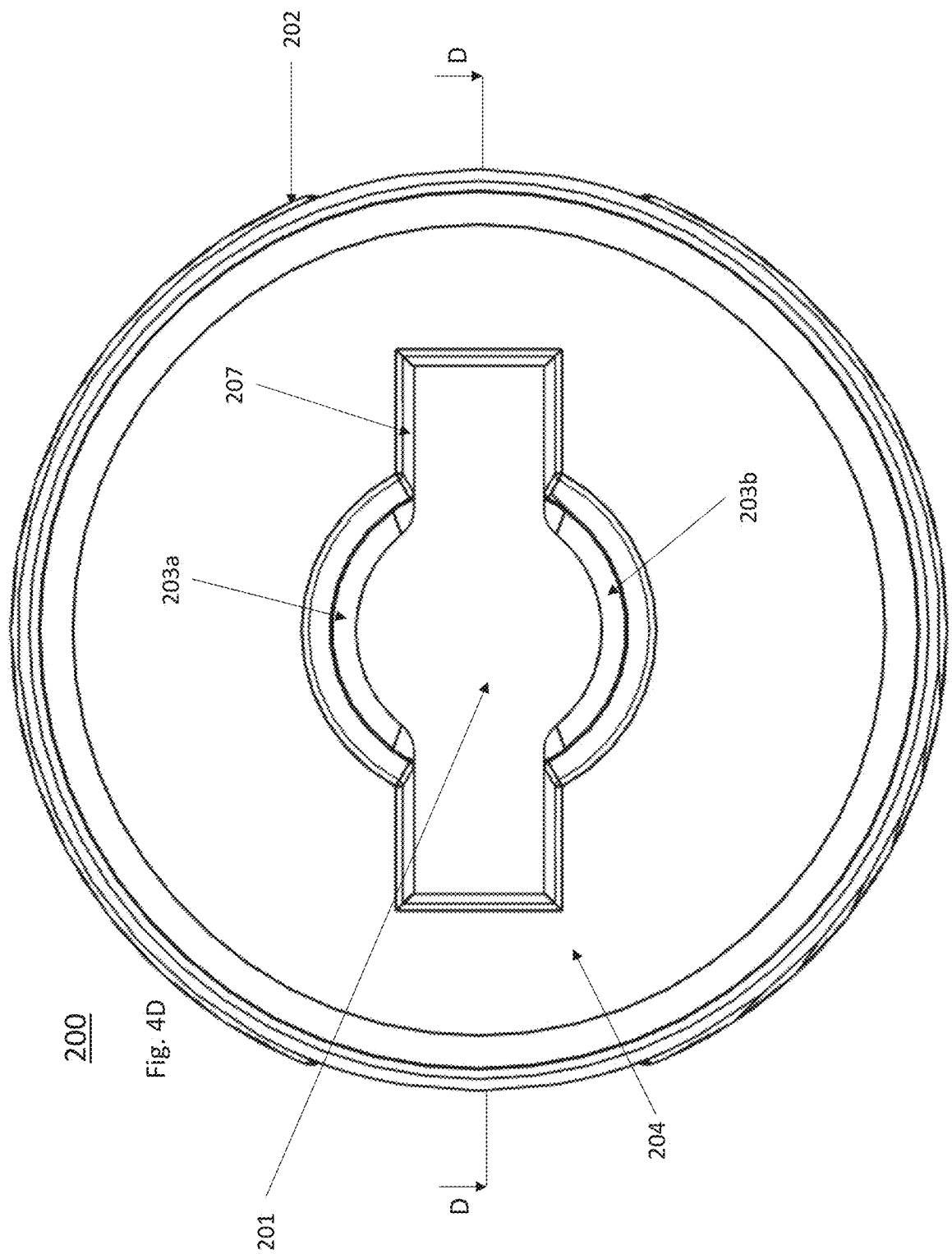

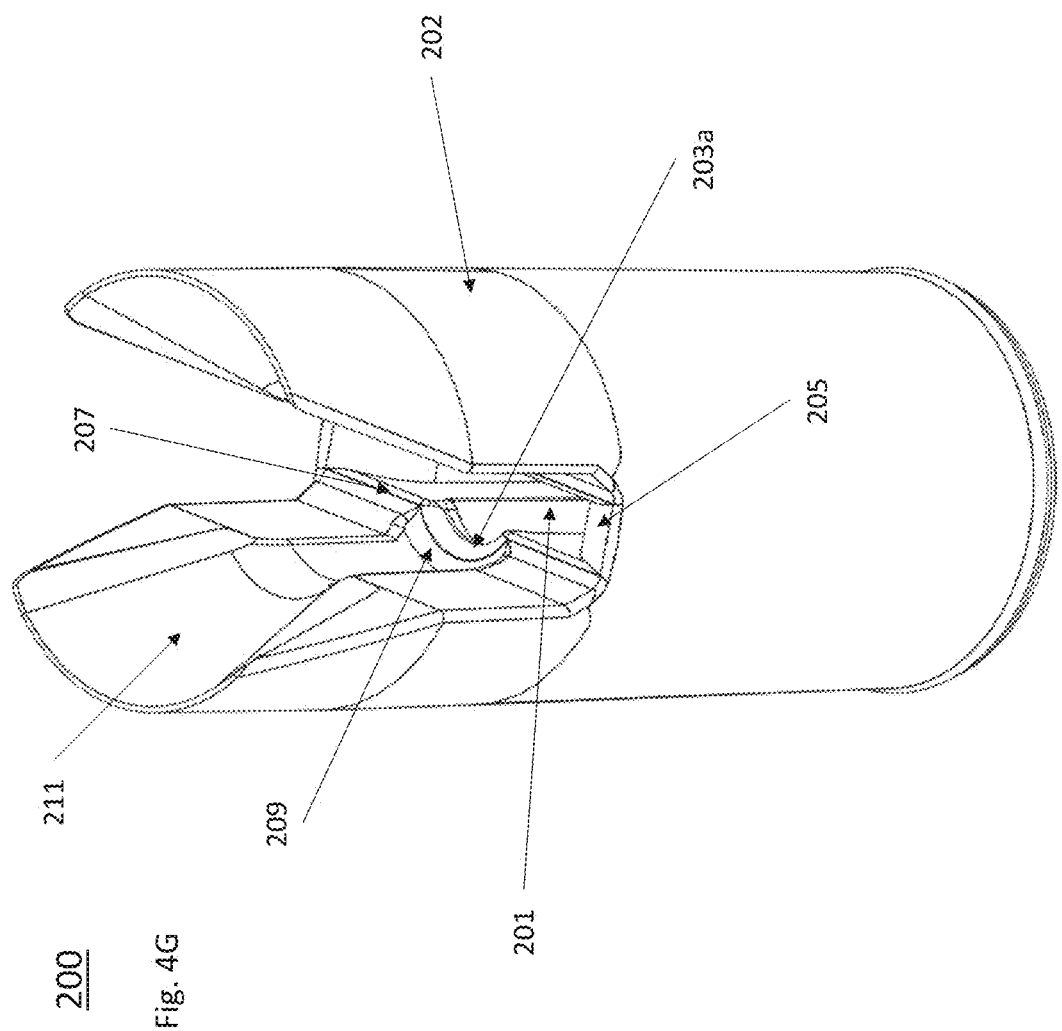

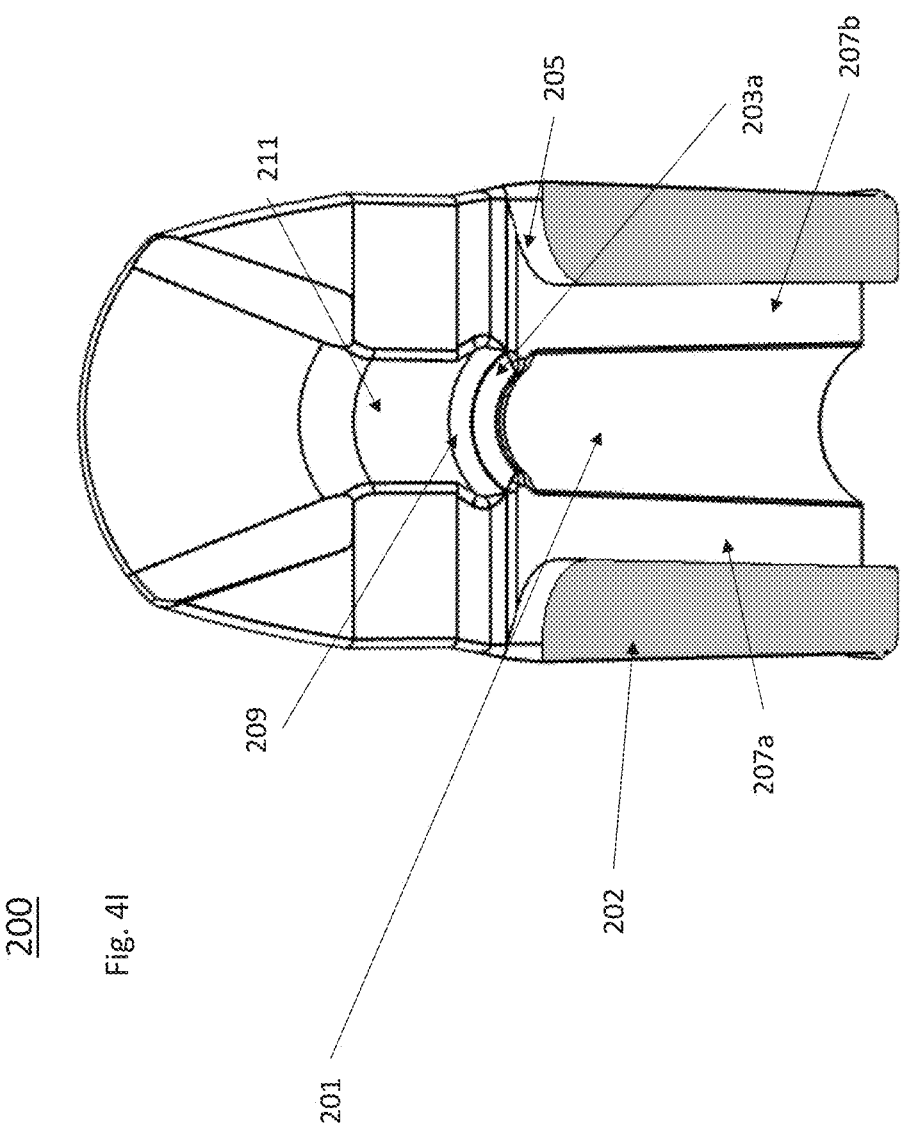

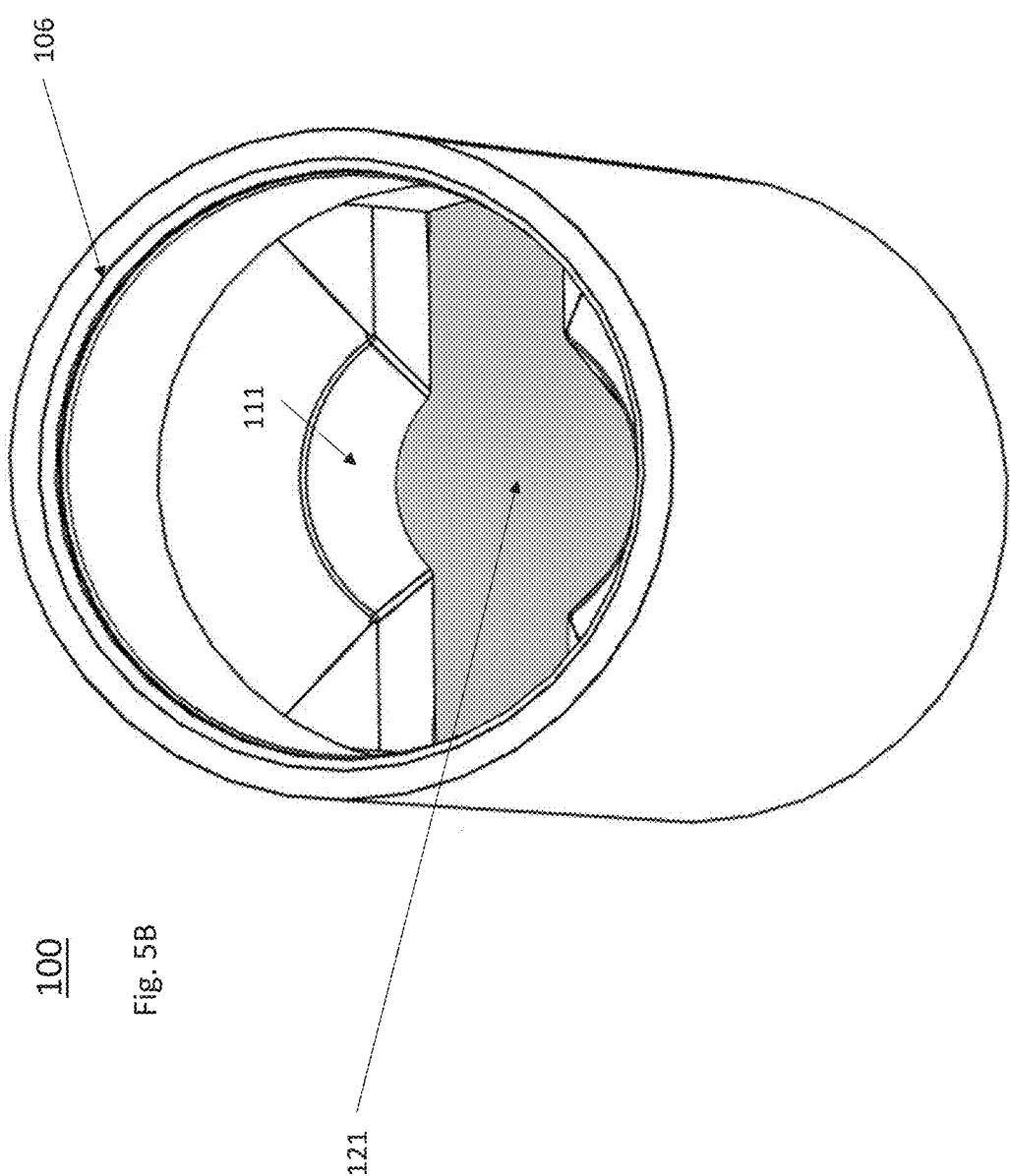

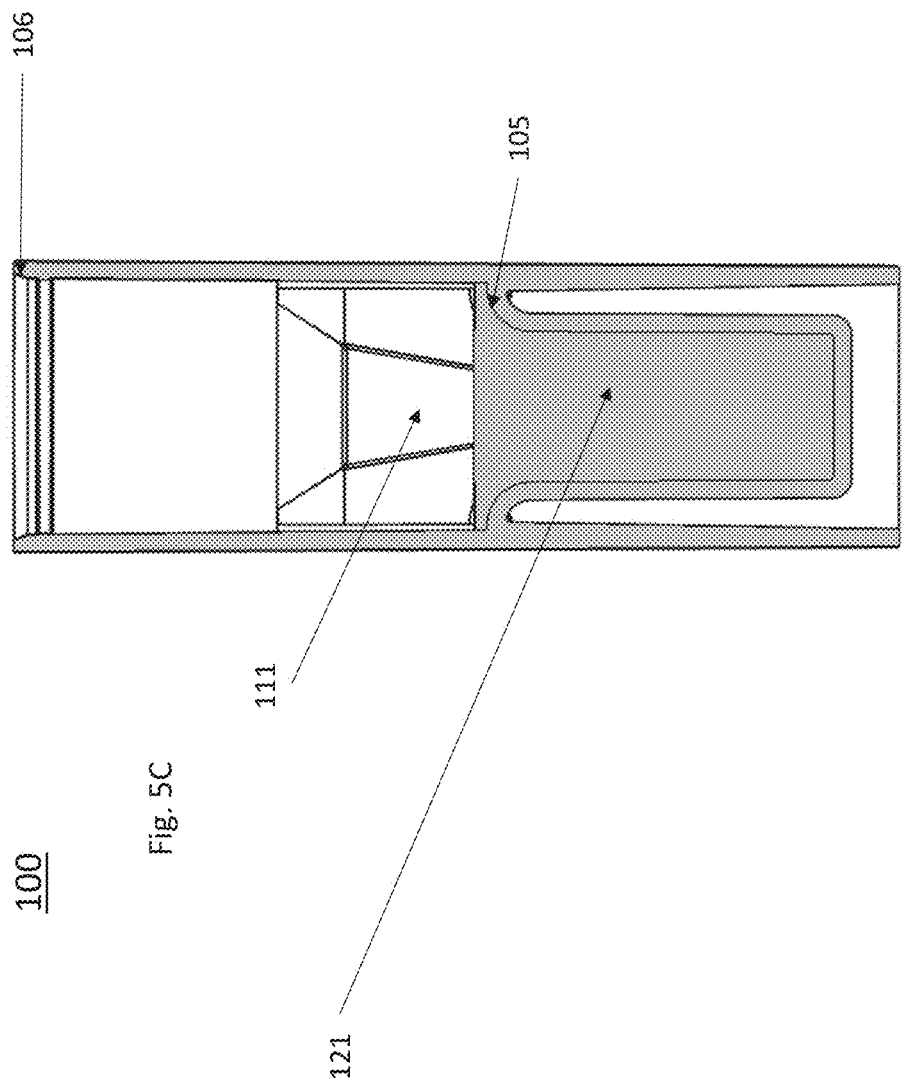

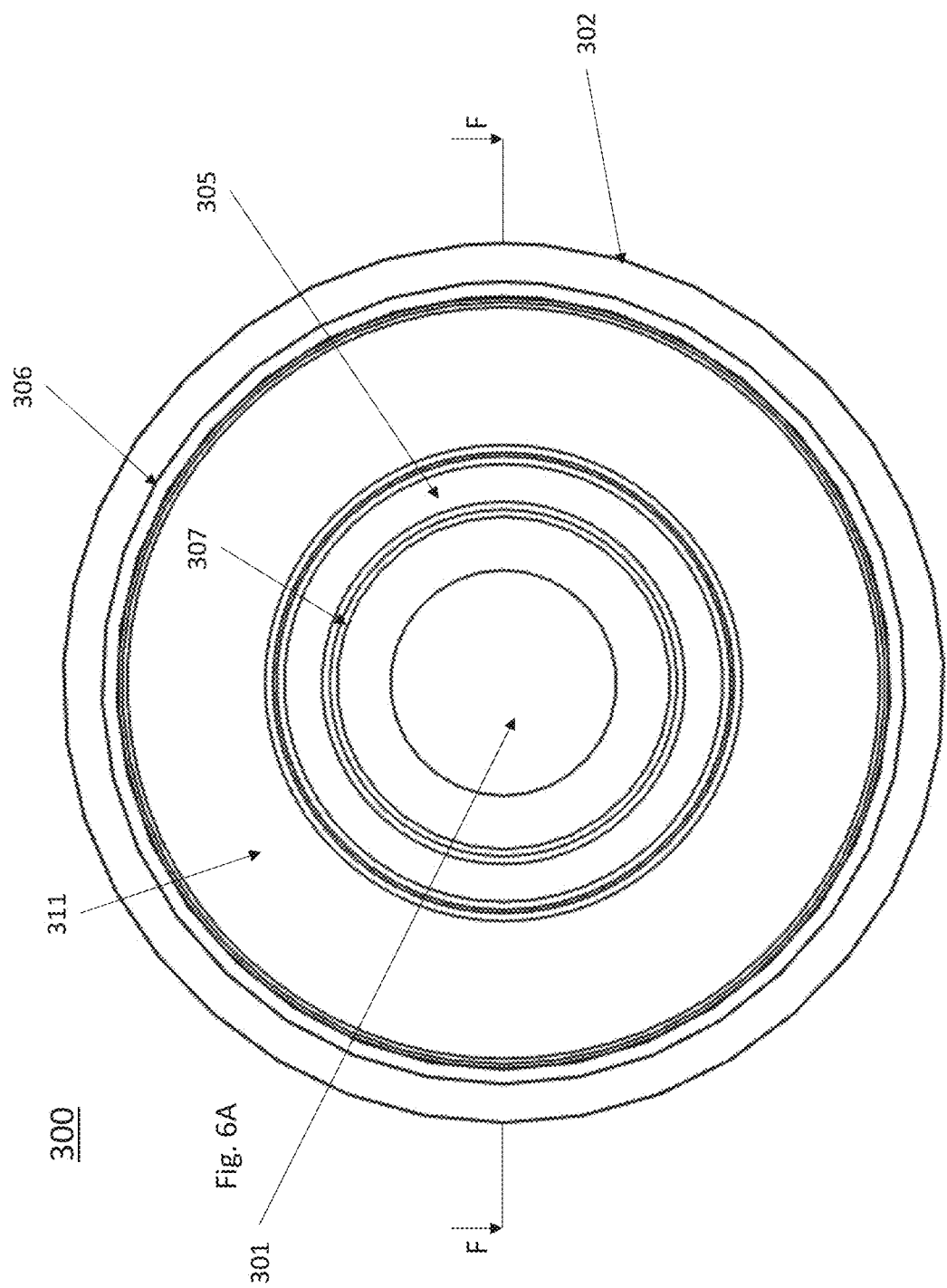

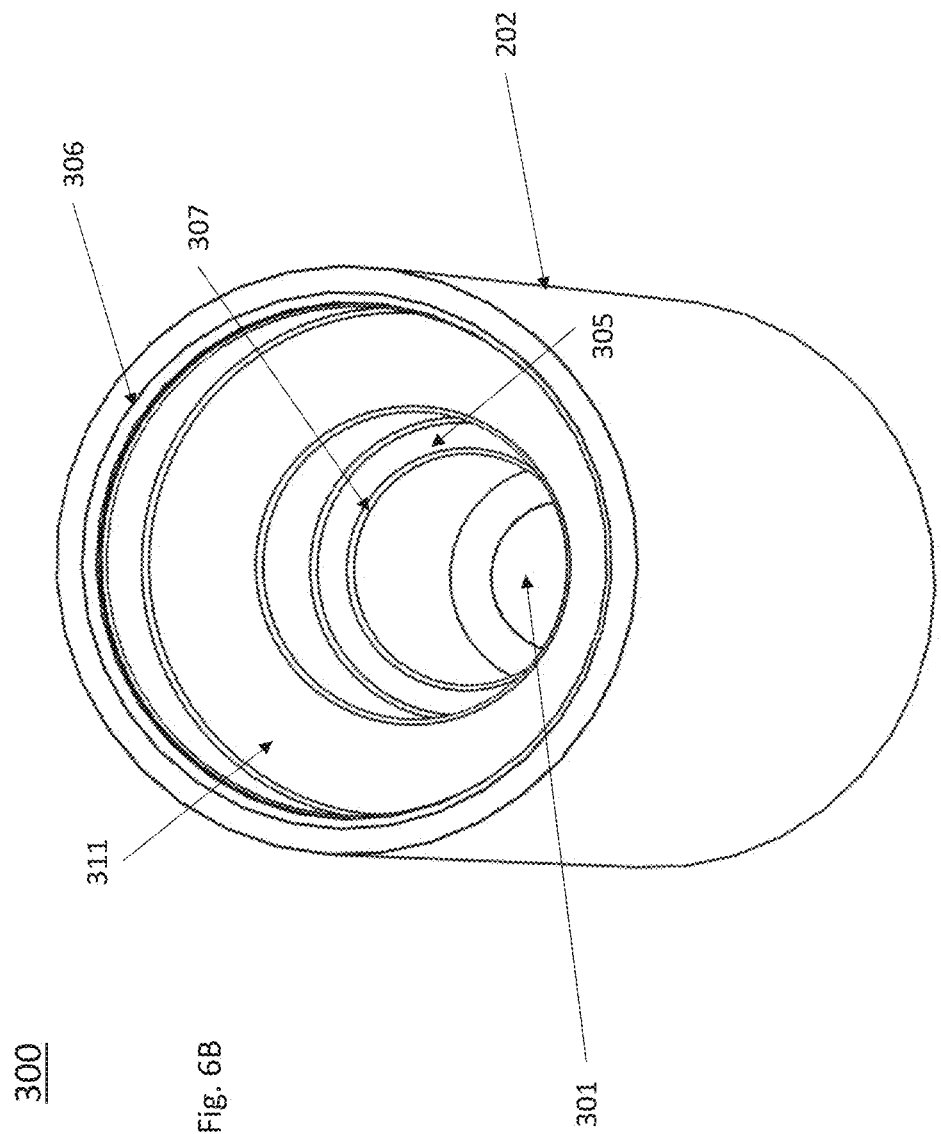

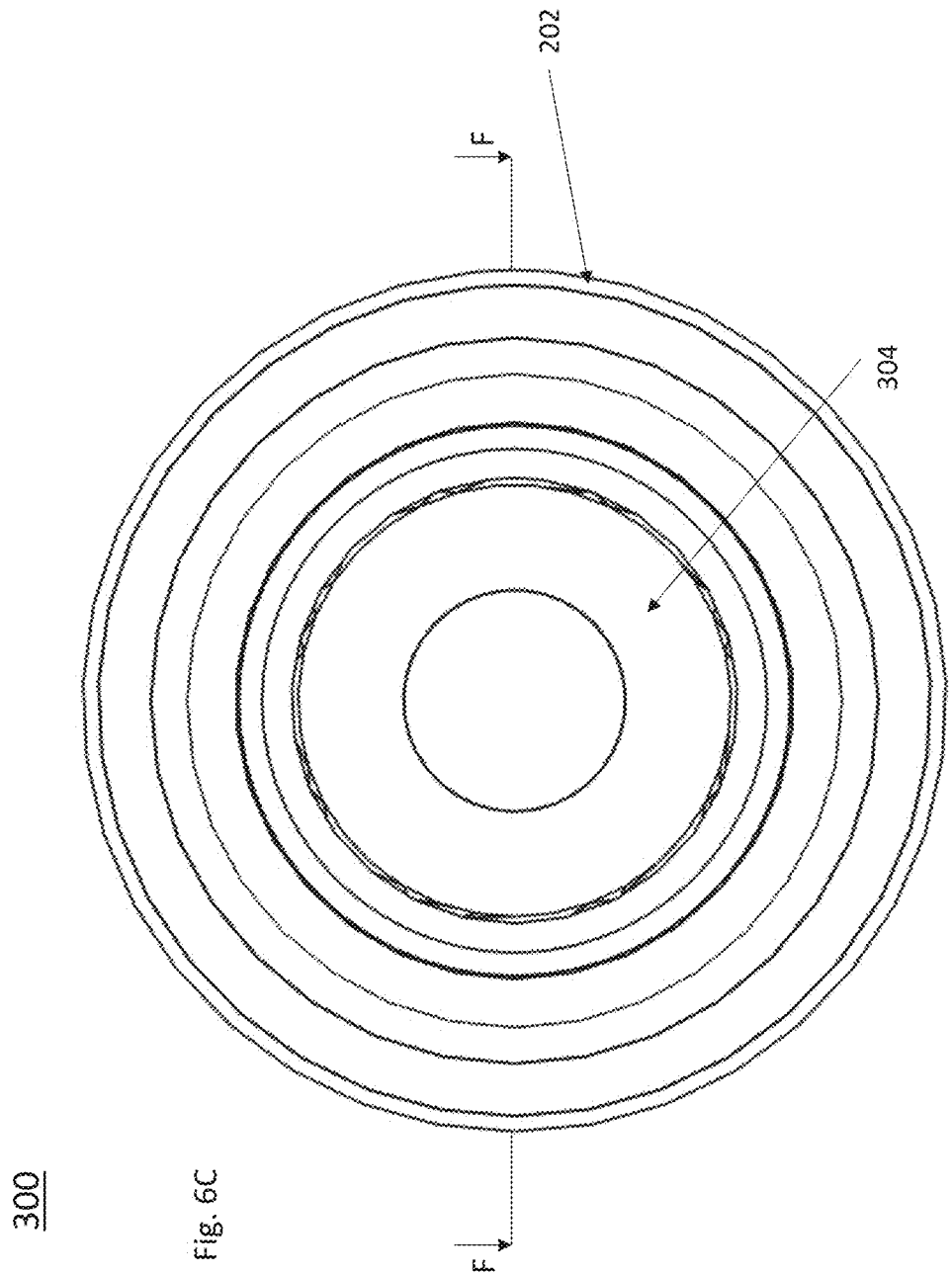

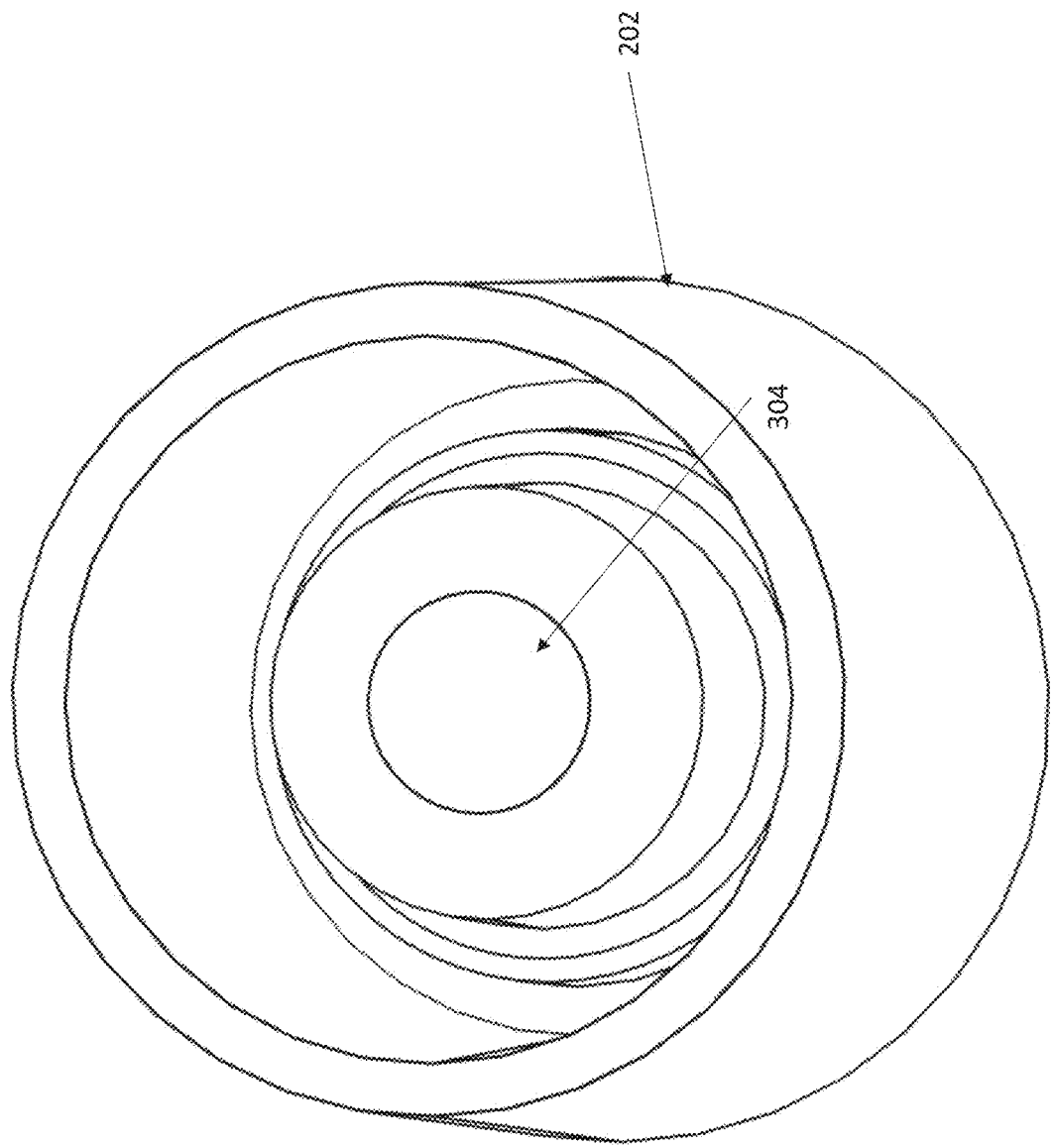

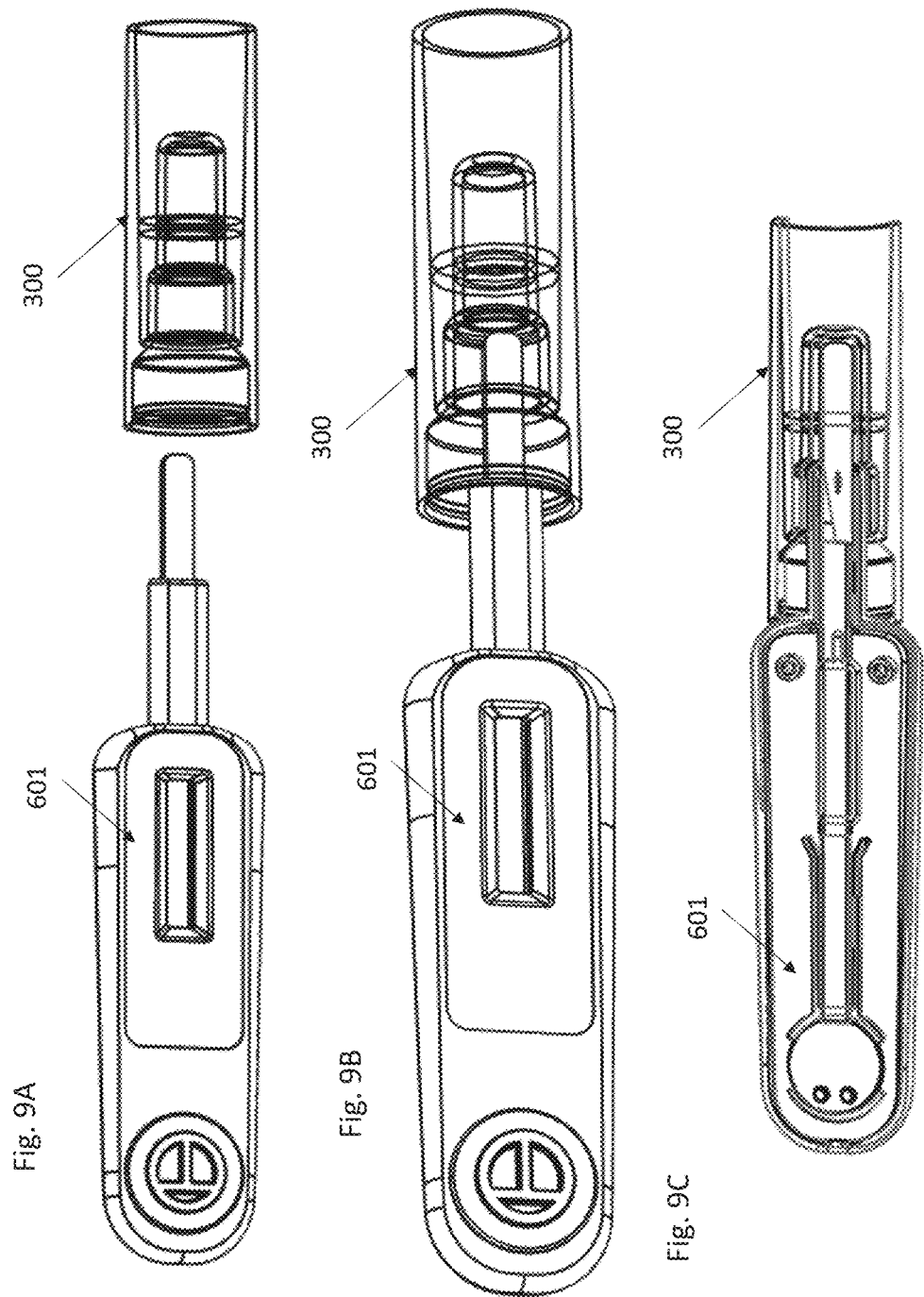

DEVELOPER SOLUTION VIAL

CROSS-REFERENCE TO RELATED APPLICATION

This application claims benefit of priority from U.S. Provisional Application No. 63/124,315 filed on Dec. 11, 2020, the entire contents of which are incorporated by reference.

TECHNICAL FIELD

This invention relates to a developer solution vial capable of use with sampling devices for biological samples such as swabs and applicators that may collect a substance from a patient, as well as assay devices incorporating such sampling devices. The developer solution vial minimizes the volume of the developer solution necessary for use in an assay device while increasing contact with the solution. By minimizing the developer solution volume, the sensitivity of the assay device may be increased due to decreased sample dilution and forcing samples onto a submerged collection pad of the assay device, thus enhancing elution efficiency of the sample entering the assay device. The developer solution vial enables point-of-care sample collection and rapid testing via low volume assay testing.

BACKGROUND

Diseases have resulted in pandemics and outbreaks throughout time. Accurate and fast diagnosis of the causative viral or bacterial pathogen is important to select the appropriate treatment, save people's lives, stop the epidemics, and reduce unnecessary use of drugs (e.g., antibiotics) in control and management of outbreaks. Point-of-care assays for detection of these respiratory and other diseases include diagnosis devices based on assay devices including assay devices in a lateral flow assay (LFA) format. LFA devices typically employ antibodies with visual detection of the endpoint immune complex formation use of recognition molecules including nanoparticle labels or aptamers. See, e.g., U.S. Pat. Nos. 7,192,555 and 6,303,081. This results in an accurate and rapid test.

LFA devices often comprise of a collection pad and an assay strip with a series of components including a blocker pad, a conjugate pad, a nitrocellulose membrane, and an absorbent pad. The assay occurs through wetting and transport of reagents as they interact with a liquid sample moving across the assay strip via a chromatographic lateral flow. The sample may be eluted from a sampling device into a developer solution which is then removed. The assay device, with the aid of the sample containing developer solution, performs the assay. The assay is performed as the liquid sample moves through the collection pad to the assay strip passing from the blocker pad to the conjugate pad to the nitrocellulose membrane and finally to the absorbent pad. Patent applications teaching the use of such typical assay devices include U.S. Pat. App. Pub. Nos. 2020/0371100 and 2010/0239458. Typical collection pads for LFA devices may include a rigid capillary matrix that can collect a sample with minimal manipulation (e.g., compression).

A developer solution facilitates elution of a sample from a sampling device (e.g., swab) and transport of the sample with the developer solution by wicking into an assay device. The same patent applications above, in particular, U.S. Pat. App. Pub. No. 2020/0371100 teaches the use of such developer solutions. One such developer solution includes an aqueous solution of surfactants, salts, preservatives, buffering agents, etc. as known in the art. Buffer agents may include phosphate, Tris-CI borate, bicarbonate, etc. Surfactants may include Tween 20, Triton X-100 or other non-ionic detergents. Preservatives may include anti-microbial and anti-fungal substances such as sodium azides.

In a typical LFA device, the liquid sample moves first to a blocker pad where assay reagents on the blocker pad are hydrated. These reagents may contain animal proteins, salts, buffers, and detergents commonly used in the diagnostic industry for inhibiting non-specific reactions (blocking) and facilitating flow. A conjugate pad stores assay reagents, such as labels and antibodies, and a signal-generating reagent, which react with a target analyte in the sample, binding to the target, as the liquid sample continues through the assay device. As the liquid sample continues along the device, binding reagents in the nitrocellulose membrane will capture the target analyte at a test line to detect the presence of the target analyte which, result in a visually present color line. Finally, the liquid sample continues to flow along a nitrocellulose membrane moving to the absorbent pad. The absorbent pad serves as the end reservoir for device fluid and wicks excess liquid. After a specified amount of time (e.g., about 1 to 10 minutes), a healthcare worker (or test administrator) or the individual (self-test) will interpret the results.

Although this method is viable for point-of-care diagnosis, large volume of developer solution of liquid bodily fluids are often needed to elute the sample and run the assay device. The need for large volumes of developer solution or for liquid bodily fluids can limit the usefulness or availability of certain tests. Also, in some cases, such as in nasopharyngeal swabbing, the sampling device needs to collect viscous samples from more uncomfortable (for the patient) locations such as the posterior nares which can be difficult to accurately assay.

Thus, there is a need for a sampling device and developer solution vial to minimize the specimen collection developer solution volume to decrease dilution of collected samples and to allow for diagnostics with a reduced sample volume, particularly those contemplated for use in point-of-care diagnosis of respiratory diseases.

SUMMARY OF THE INVENTION

The invention provides a developer solution vial and methods of its use to diagnose diseases using a collection and/or assay device, for example, for use with a lateral flow assay (LFA) device. The developer solution vial may include any container that is capable of holding developer solution. The developer solution vial is keyed to the collection and/or assay device. In other words, the developer solution vial provides an interior surface that coordinates with a portion of sampling and/or assay devices to rest the device(s) in the developer solution vial while preventing compression of the heads of the sampling and/or assay devices after fully inserting the devices. The developer solution vial provides an accurate, sensitive, and rapid test without as much patient discomfort by reducing sample dilution for smaller sample volumes. The developer solution vial does this by minimizing the use of developer solution while providing greater depth for sampling devices and assay devices such as LEAs into the developer solution.

For example, for nasal fluid applications, collecting respiratory samples is often conducted through use of a swab from individuals suspected of having signs and symptoms of an acute respiratory disease. A healthcare professional or the patient themselves will swab both anterior nares and transfer the specimen to the developer solution vial for testing with the LFA. Commonly, a developer solution that is a dilution buffer is required to free samples from a specimen on a swab. Collection from the anterior nares reduces discomfort, but generally provides less concentrated samples. Thus, the developer solution vial may increase sensitivity of the assay device, by reducing the volume of developer solution used to reduce diluting the collected sample.

Although the invention is described with respiratory diseases as an exemplary target embodiment, use of the same sampling and assay devices and developer solution vials may be applicable for any point-of-care diagnosis, such as for surface sampling or sampling of other bodily fluids.

Accordingly, the invention relates to a developer solution vial for use with an assay device to minimize use of developer solution with increased sampling device contact in the developer solution. The developer solution vial includes a reduced volume cavity for developer solution storage. The developer solution vial includes mating portion for interface and use with sampling and assay devices during testing.

The invention further relates to a method of using the developer solution vial in diagnosing diseases.

BRIEF DESCRIPTION OF THE DRAWINGS

FIG. 2B is an exemplary bottom perspective view illustration of a developer solution vial for use with an assay device, of the invention.

FIG. 3A is an exemplary cross-sectional front view illustration of a developer solution vial of FIGS. 1A and 2A for use with an assay device from section C-C of one embodiment of the invention.

FIG. 3B is an exemplary cross-sectional front perspective view illustration of a developer solution vial of FIGS. 1A and 2A for use with an assay device from section C-C of one embodiment of the invention.

FIG. 4A is an exemplary top view illustration of a developer solution vial insert for use with an assay device, of the invention.

FIG. 4B is an exemplary top perspective view illustration of a developer solution vial insert for use with an assay device, of the invention.

FIG. 4C is an exemplary top-side perspective view illustration of a developer solution vial insert for use with an assay device, of the invention.

FIG. 4D is an exemplary bottom view illustration of a developer solution vial insert for use with an assay device, of the invention.

FIG. 4G is an exemplary side perspective view illustration of a developer solution vial insert for use with an assay device, of the invention.

FIG. 4I is an exemplary cross-sectional front perspective view illustration of a developer solution vial insert of FIGS. 4A-4G for use with an assay device from section D-D of one embodiment of the invention.

FIG. 5B is an exemplary top perspective view illustration of a developer solution vial filled with developer solution for use with an assay device, of the invention.

FIG. 5C is an exemplary cross-sectional front view illustration of a developer solution vial for use with an assay device from section E-E of one embodiment of a developer solution vial of FIG. 5A of the invention.

FIG. 6A is an exemplary top view illustration of a minimized developer solution vial for use with an assay device, of the invention.

FIG. 6B is an exemplary top perspective view illustration of a minimized developer solution vial for use with an assay device, of the invention.

FIG. 6C is an exemplary bottom view illustration of a minimized developer solution vial for use with an assay device, of the invention.

FIG. 6D is an exemplary bottom perspective view illustration of a minimized developer solution vial for use with an assay device, of the invention.

FIG. 9A-D are exemplary front view illustrations of a direct sample collection pad in use with the minimized developer solution vial, of the invention.

DETAILED DESCRIPTION OF THE INVENTION

The invention provides a reduced volume developer solution vial for collecting samples for use with an assay device, and methods of use that simplify and make more efficient diagnostics of respiratory diseases, including a number of viruses (approximately 80% of all respiratory diseases being viral) such as influenza A and B viruses, parainfluenza virus (PIV) type 1 (PIV1), PIV2, PIV3, respiratory syncytial virus (RSV), adenovirus, rhinovirus, avian influenza viruses (H5N1, H7N7, and H7N3), human metapneumovirus (hMPV), severe acute respiratory syndrome (SARS), coronavirus (COVID-19), bocavirus, enterovirus, PIV4, parvovirus types 4 and 5, and mimivirus all affect the respiratory tract. Although discussed below in view of exemplary embodiments of the invention that may refer specifically to COVID-19, the invention may be used for any number of sampling collection methods for disease diagnosis, including, for example, sample collection by swabbing from surfaces or a patient's bodily fluid. Although the description of the invention may refer specifically to nasal sample collection, the collection of samples may include saliva sampling, other sampling of bodily fluids, or sampling from surfaces. The invention may generally be used in a point-of-care sample collecting and rapid testing method via low-volume fluid flow assay testing.

COVID-19 Lateral Flow Assays

Immunoassays are being employed on the front-lines to determine whether or not a person has COVID-19 or been exposed to it. Positive results from an immunoassay indicate the presence of SARS-1 and SARS-2 Nucleocapsid Antigen. Clinical correlation with patient history and other diagnostic information is necessary to determine patient infection status. Positive results are presumptive and require additional testing to confirm the presence of SARS-CoV-2 antigens that cause COVID-19 disease. Positive results do not rule out bacterial infection or co-infection with other viruses. Negative results do not preclude SARS-CoV-2 infection and are not used as the sole basis for patient management decisions. Negative results must be combined with clinical observations, patient history, and epidemiological information.

A developer solution vial of the invention may be used with a LFA device to test for COVID-19. Such a LFA device typically has a collection pad used in a COVID-19 rapid antigen test as an in vitro diagnostic single-use immunoassay for qualitative detection of SARS-1 and SARS-2 Nucleocapsid Antigen in nasal sample collected from the anterior nares in individuals who meet the COVID-19 clinical and/or epidemiological criteria.

Developer Solution Vial

Figure 1A:
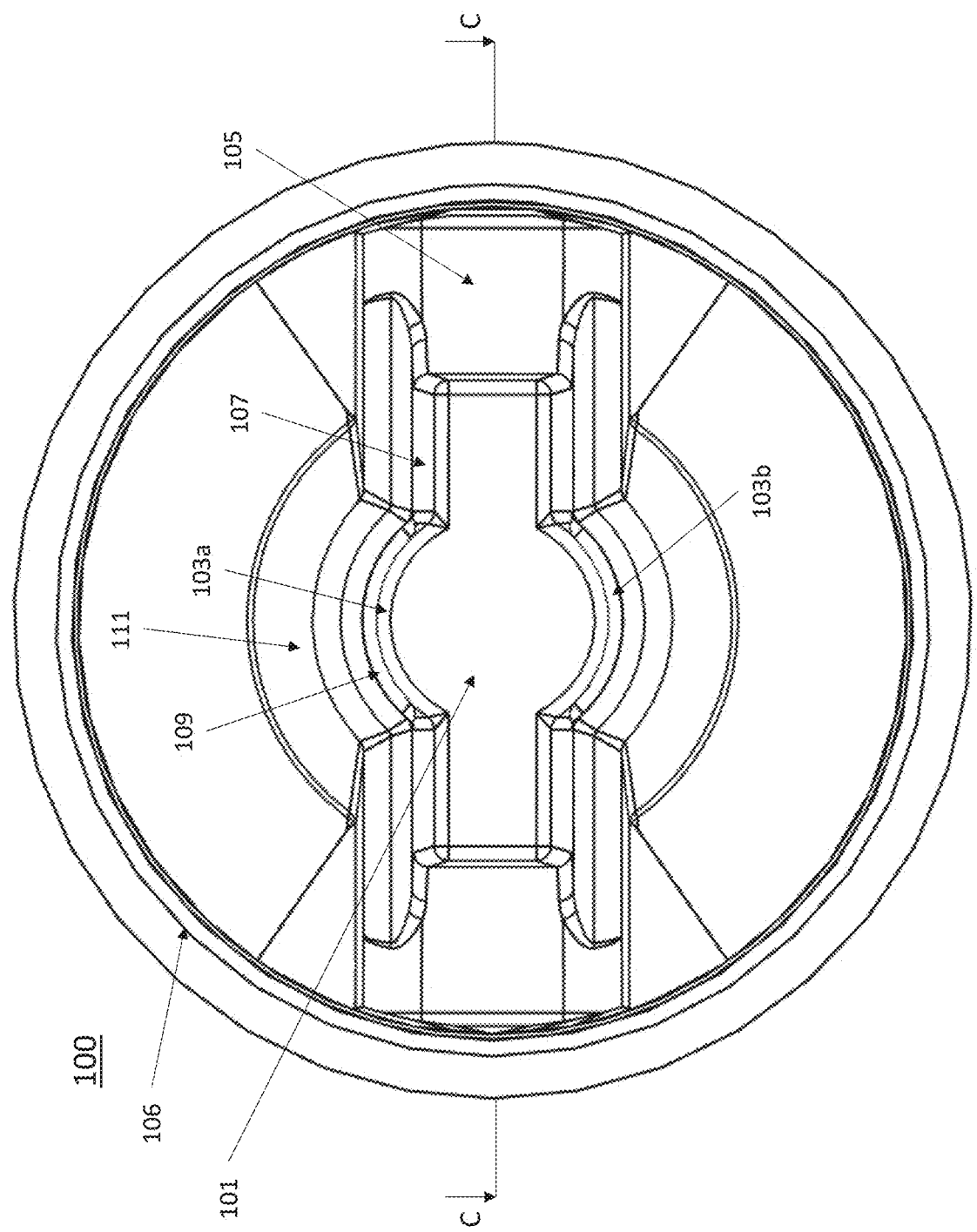
FIG. 1A is an exemplary top view illustration of a developer solution vial for use with an assay device, of the invention.
Figure 1B:
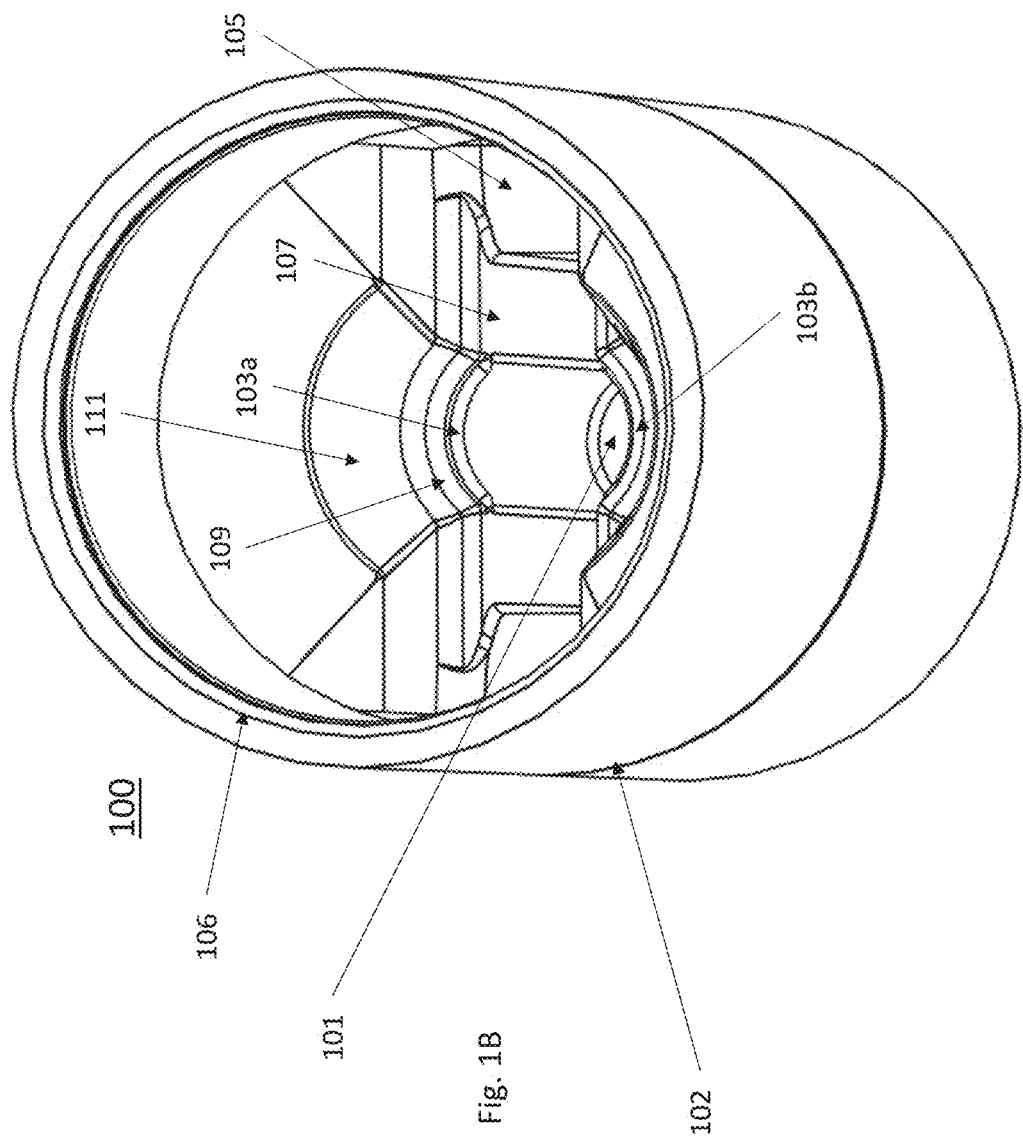
FIG. 1B is an exemplary top perspective view illustration of a developer solution vial for use with an assay device, of the invention.
Figure 1C:
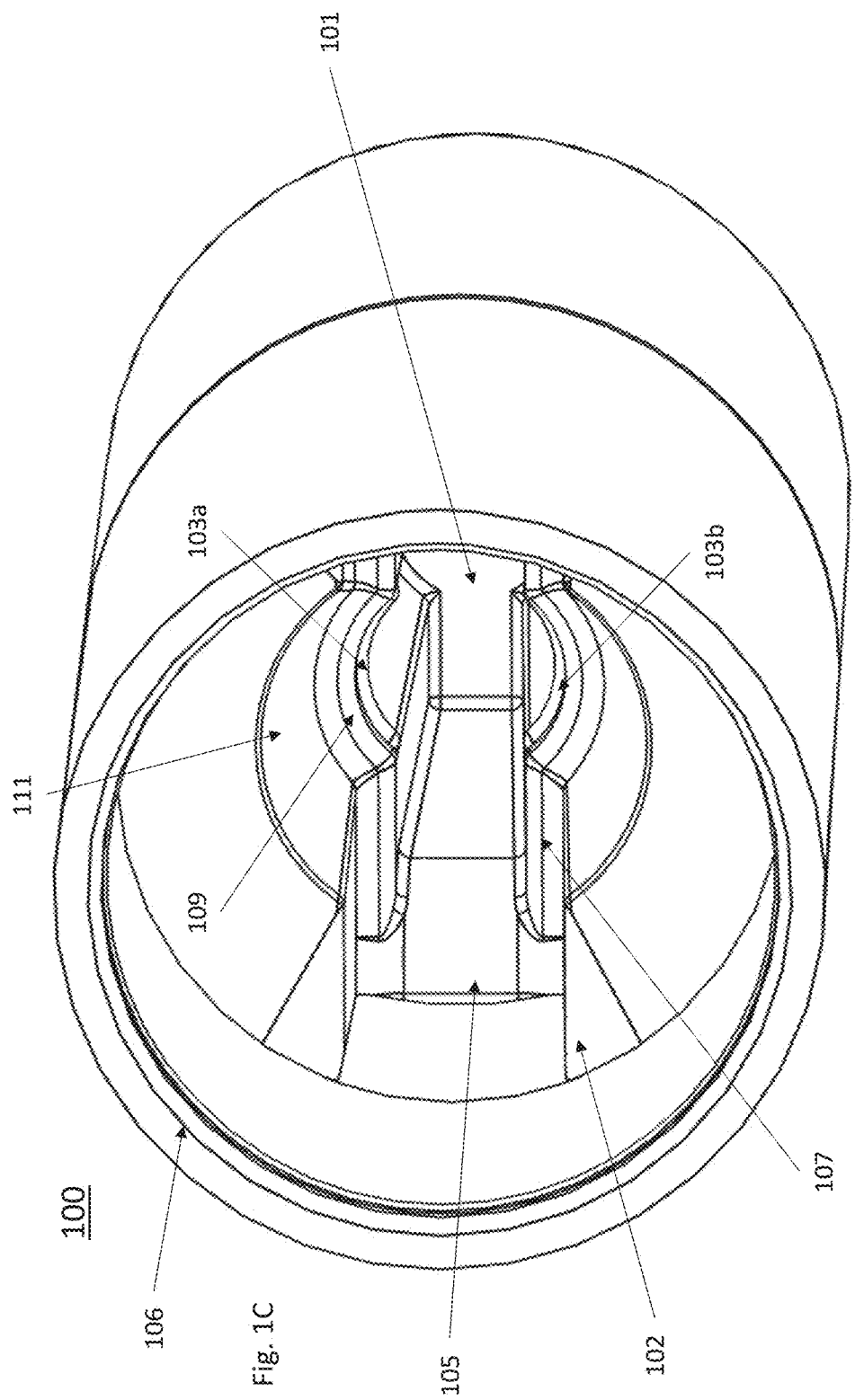
FIG. 1C is an exemplary top-side perspective view illustration of a developer solution vial for use with an assay device, of the invention.

FIG. 1A-1C show exemplary top, top perspective, and top-side perspective view illustrations of a developer solution vial for use with an assay device, of the invention. The developer solution vial 100 is keyed to and used with sampling devices and assay devices for use in diagnostics testing for a respiratory disease. The sampling devices may include swabs and other applicators. A swab may include a cotton swab or flat swab with different shapes and sizes. The assay devices may include LFAs or other fluid assay devices. In some embodiments, the sampling device, such as a rigid capillary matrix, is integrated into the assay device to reduce the number of devices used and steps required for diagnosis. Although the sampling devices described below may reference a swab, any sampling device may be used and appropriately fitted or keyed to the developer solution vial 100 so that the two mate.

The developer solution vial 100 may be a single piece device or fit together as an insert with a defined cavity 101 and elongated housing 102 including a mating portion 131 (see, e.g., FIG. 3A) for interfacing with sampling and assay devices. The housing 102 may include any number of outer shapes and sizes, such as a cylinder, rectangular prism, triangular prism or other prism shapes including star shaped, or other asymmetrical shape prisms. The housing 102 includes an opening 106 extending to cavity 101. However, the cavity 101, in an exemplary embodiment, is reduced in volume to minimize the dilution of a collected sample. The volume of the cavity may range from 75 to 1500 microliters (µL). In some embodiments, the volume of the cavity is preferably between 450 and 850 µL. In some embodiments, the volume of the cavity s preferably between 600 and 750 µL. The cavity 101 may contain a stabilizing developer solution. The volume of developer solution is between 50 and 1000 microliters. In some embodiments, the volume of developer solution is preferably between 300 and 450 microliters. In some embodiments, the volume of developer solution is preferably between 400 and 450 microliters. The elongated housing 102 includes, surrounding the cavity 101, a mating portion 131. The mating portion 131 includes extraction portion 103a and 103b, seating portion 105, and sidewall portion 107, sampling device interface portion 109, and guiding wall portion 111.

The extraction portion 103a and 103b protrudes from the sampling device interface portion 109 toward a center of the cavity 101. The exemplary extraction portion 103a and 103b shown in the figure has a rounded semi-circular cross-sectional shape that protrudes into the cavity 101. The extraction portion 103a and 103b aids in the recovery of collected sample and developer solution which remains in a swab as the swab is removed from the developer solution vial 100. Each pass of the swab through the extraction portion 103a and 103b may recover more collected sample from the swab. Because swabs generally include a circular shape, the sampling device interface portion 109 and the extraction portion 103 generally have a circular shape and is sized just large enough to compress and allow the swab to enter the cavity containing the developer solution. In some embodiments, the extraction portion 103a and 103b may be a single-piece unit with the rest of the developer solution vial 100. In other embodiments, the extraction portion 103a and 103b is a separate part added to the developer solution vial 100. The extraction portion 103a and 103b may be shaped to engage with any particular sampling device and may also be considered a squeegee for the sampling device to recover sample from the sampling device for depositing into a developer solution in the developer solution vial 100.

In some embodiments, the extraction portion 103a and 103b may be a single continuous part in instances where the assay device is of a similar or same shape as the extraction portion 103. In some embodiments, the extraction portion 103 may include a plurality of parts spread evenly around the perimeter of the cavity to provide even extraction of the sample from a sampling device. In some embodiments, the extraction portion 103 may include rough or abrasive features along the surface of the extraction portion 103 to aid in recovery of sample from the sampling device.

In some embodiments, the extraction portion 103 may include a protruding triangular shape or other shape that further promotes recovery of sample from the sampling device and developer solution that may remain on the sampling device. The extraction portion 103 may also promote entry into the cavity 101 by requiring a greater force from a user to remove the sampling device rather than insert the sampling device. This may be done through a biased or multiple inclined extraction portion that has a more gradual incline for insertion into the cavity 101 and a more drastic incline for removal to prevent accidental removal and aid in recovery.

The seating portion 105 is configured to allow the collection pad of an assay device to rest in the developer solution vial 100. The seating portion 105 includes a mating surface to contact a resting surface of the housing or the collection pad of the assay device. The contacting surfaces allow the assay device to rest in the developer solution vial 100 without touching the both the bottom of the cavity 101 and sidewalls of the cavity 101 of the developer solution vial 100 which prevents compression. The resting surface may include one or more surfaces of an outer boundary of the assay device. In some embodiments, the resting surface includes a widest cross-sectional portion of the assay device near the collection pad. For example, as shown in FIGS. 8A-D, the widened portion of the collection pad and housing provides a resting surface 403 for the assay device in the developer solution vial 100. Thus, the mating surface generally contours with the resting surface of the assay device to place the assay device in a centered location when resting in the developer solution vial 100.

The interior walls of the mating portion 131 help to define cavity 101 include the sidewall portion 107, sampling device interface portion 109, and guiding wall portion 111. The sidewall portion 107 is configured to allow the front and back planar portions of the collection pad to be evenly placed in the developer solution vial 100 without compression of the collection pad. In some embodiments, the sidewall portion 107 may include contours to permit particular collection pads of a predetermined shape and size to interface with the developer solution vial 100. The sidewall portion 107 provides structure to the cavity 101 to allow the collection pad to, when resting in the developer solution vial 100, enter the cavity 101 and sit without touching the sidewall portion 107. The sidewall portion 107 defines the cavity 101 to minimize the volume of developer solution in the developer solution vial 100 by providing a minimal space between the collection pad and sidewall portion 107 while still allowing sample to be drawn into the collection pad.

The interior walls of the mating portion 131 may generally include a slightly angled shape to guide any sampling device or assay in towards the center of the cavity 101. Although separately depicted, the sampling device interface portion 109 may also be incorporated into the guiding wall portion 111 to further aid in the sample recovery and guiding of the sampling device into the developer solution stored in the cavity 101. The sampling device interface portion 109 is contoured to the shape and size of a predetermined sampling device. In some embodiments, the sampling device is a swab with a circular shaped head and thus the sampling device interface portion 109 is also in a circular shape. The sampling device interface portion 109 may also define the shape of the extraction portion 103a and 103b, where the extraction portion 103a and 103b includes a concentrically contoured surface to the sampling device interface portion 109.

In the exemplary embodiment shown, the guiding wall portion 111 includes a smaller incline from vertical than the sampling device interface portion 109. The guiding wall portion 111 is a much longer, longitudinally, portion than the sampling device interface portion 109. As a sampling or assay device is guided into the developer solution vial 100, the interior walls of the mating portion 131 begin to slowly force (with the guiding wall portion 111), the sampling or assay device, in toward the center of a volume of solution contained in the bottom of the cavity 101 of the developer solution vial 100, however as the cross-sectional area defined by the guiding wall portion 111 reduces, the sampling device will meet a extraction portion 103a or 103b which is slightly smaller than the width of a head of the sampling device. This forced contact with the extraction portion 103a or 103b aids recovery of any samples collected on the sampling device into the developer solution through a compressive and/or friction force. The guiding wall portion 111 may begin between the opening 106 and a top edge of seating portion 105 to help guide the sampling or assay device into the developer solution vial without resting on the bottom of the developer solution vial 100.

Figure 2A:
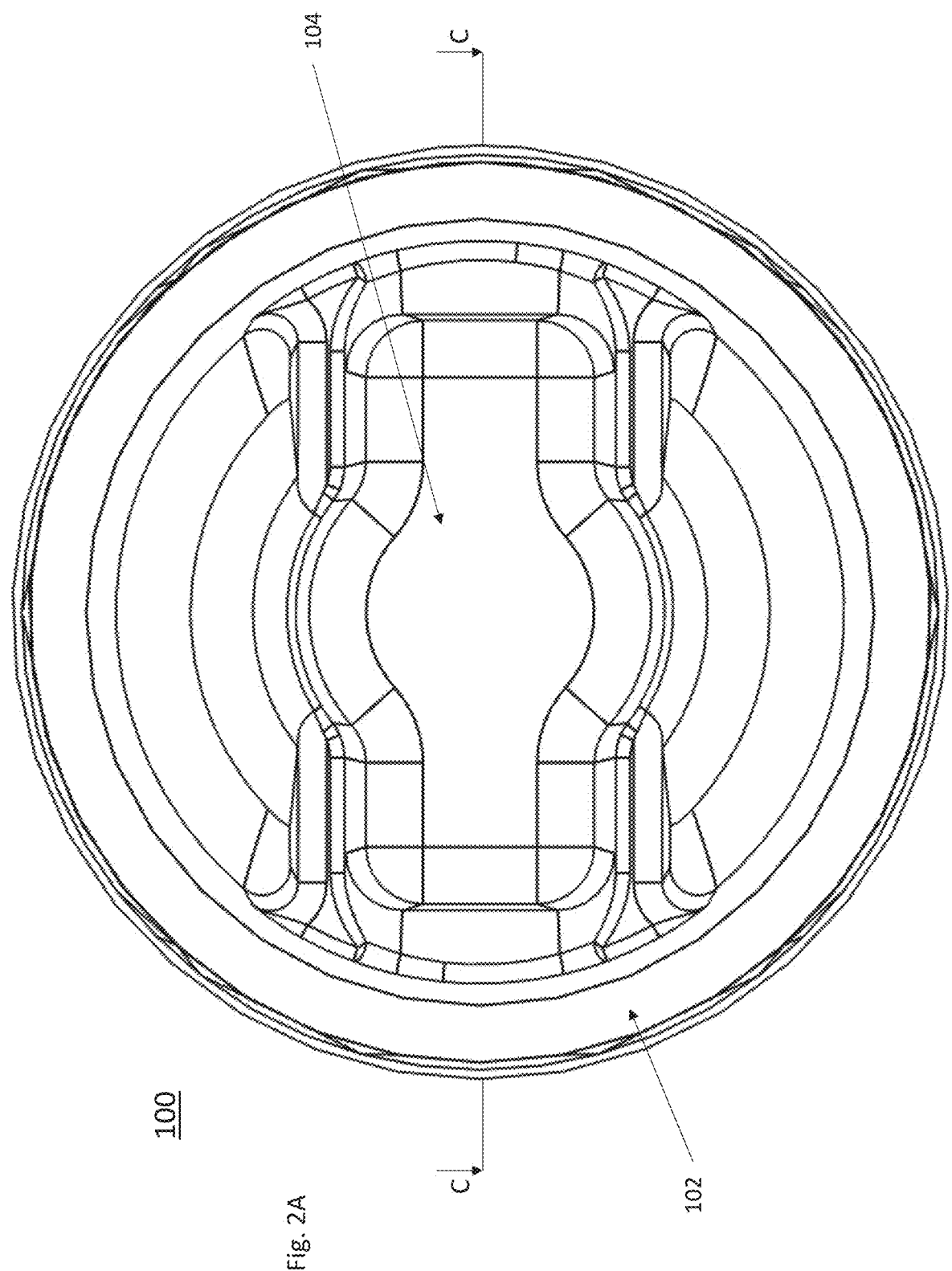
FIG. 2A is an exemplary bottom view illustration of a developer solution vial for use with an assay device, of the invention.

FIGS. 2A and 2B show exemplary bottom and bottom perspective view illustrations of a developer solution vial for use with an assay device, of the invention. The exemplary developer solution vial 100 may be injection molded or manufactured in other ways. An injection molded developer solution vial may include a contoured bottom interior corresponding to the cavity 101, however, the base 104 provides the developer solution vial 100 a support to retain the sampling or assay device, when at rest, in an upright position. The sampling or assay device is retained longitudinal to the elongated housing 102 using the elongated housing 102 sidewalls and/or the bottom planar face of the vial 100. The base 104 prevents tipping of the developer solution vial 100 when a sampling or assay device is rested in the developer solution contained in the developer solution vial 100. When used in conjunction with a testing stand, the developer solution vial 100 is capable of retaining the sampling or assay device, when in a resting state, in a vertical or near vertical position to aid in user agitation of a sample in the developer solution and allow the assay device to drive (by wicking) the sample through the assay device on its own, i.e., through adsorption and capillary action.

FIGS. 3A and 3B show exemplary cross-sectional front and cross-sectional front perspective view illustrations of a developer solution vial for use with an assay device from section C-C of one embodiment of a developer solution vial of FIGS. 1A and 2A, of the invention. The cross-sectional view shows longitudinal length of walls inside the cavity 101 more clearly. The sidewall portions 107a and 107b help to define a key-hole shaped opening holding the developer solution. The sidewall portions 107a and 107b are nearly vertical to guide the sides of an assay device into the cavity 101. The sidewall portions 107a and 107b are from the bottom of the cavity 101 to an area near the extraction portion 103a of the to help define the central part of the developer solution vial 100, where the developer solution is contained and samples are collected and drawn. When in a resting position in the developer solution vial 100, the sampling or assay device will rest on the seating portion 105. Thus, the seating portion 105 is configured to mate with the side structure of a sampling or assay device to retain the device in an upright position in the developer solution vial 100 without user support. When resting, a head of the sampling or assay device (for sample collection and/or flow of sample into the assay) will preferably not be compressed by or touch the sidewalls and the bottom of the cavity to create consistent flow into the assay and enhance elution efficiency.

The guiding wall portion 111 may include multiple sections where a first section 108, nearer the opening 106, may include a more angled, from vertical, wall shape, and a second section 110, nearer the top of the extraction portion 105, may include a less angled, from vertical, wall shape. Although the developer solution vial 100 may depict the first section 108 to be shorter, longitudinally, than the second section 110, any longitudinal length for each section that helps to guide sampling or assay devices into the cavity 101 may be appropriate. As long as the first section 108 is wider, cross-sectionally, than the second section 110.

In some embodiments, the extraction portion 103a may be located lower (closer to the bottom of cavity 101) or higher (nearer the top of the seating portion 105 or even into the guiding wall portion 111) in the cavity 101. However, the position of the extraction portion 103a would be based on the length of a head of the sampling device, and ideally remain below the top of the seating portion 105 to provide access to the extraction portion 103a while the sampling or assay device is submerged in the developer solution.

FIGS. 4A-4C show an exemplary top, top perspective, top-side perspective view illustrations of a developer solution vial insert for use with an assay device of the invention. The developer solution vial insert 200 may include, as shown, cavity 201 and elongated housing 202 with mating portion 231 (see, e.g., FIG. 4H) for interfacing with sampling and assay devices. The mating portion 231 is keyed to the size and shape of the sampling and assay devices to be used. The mating portion 231 includes, extraction portion 203a and 203b, seating portion 205, sidewall portion 207, sampling device interface portion 209, and guiding wall portion 211. The mating portion 231 of the developer solution vial insert 200 surround cavity 201 and interface with sampling or assay devices. The mating portion 231 helps guide the sampling or assay device into the developer solution vial assembly (the assembled developer solution vial insert 200 and elongated housing) when in use. The mating portion 231 of the developer solution vial insert 200 define cavity 201 and guide the sampling or assay device into the developer solution vial assembly (the assembled developer solution vial insert 200 and elongated housing) when in use. The mating portion 231 have similar features as described by the developer solution vial 100 of FIGS. 1A-3B above.

The developer solution vial insert 200 does not include outer sidewalls and thus more clearly shows the contoured shape for mating with predetermined sampling and assay devices. FIG. 4D shows an exemplary bottom view illustration of the developer solution vial insert of FIGS. 4A-4C for use with an assay device, of the invention. As shown, cavity 201 runs through the whole of the developer solution vial insert 200 with a base 204 on one end and the keyed opening top at the other end. The amount of developer solution required for use with the insert is then based on a corresponding container for which the developer solution vial insert 200 is combined. The corresponding container may include labware such as glass tubes, conical vials, or other container or enclosure. The corresponding portion of the corresponding container further defining the boundaries of the combined cavity (the cavity 201 and space between the base 204 and bottom of the corresponding container), and thus define the volume of developer solution used with the developer solution vial insert 200. In some embodiments, the cavity 201 may be closed on the end with base 204 to further restrict the amount of developer solution needed to fill cavity 201. However, the combined cavity is preferably sized to provide a specific minimized volume of developer solution for use. The cross-sectional width of the developer solution vial insert 200 is then predetermined to tightly fit the corresponding container to prevent additional developer solution from seeping out from any space between the developer solution vial insert 200 and the inside surface of the corresponding container.

Figure 4E:
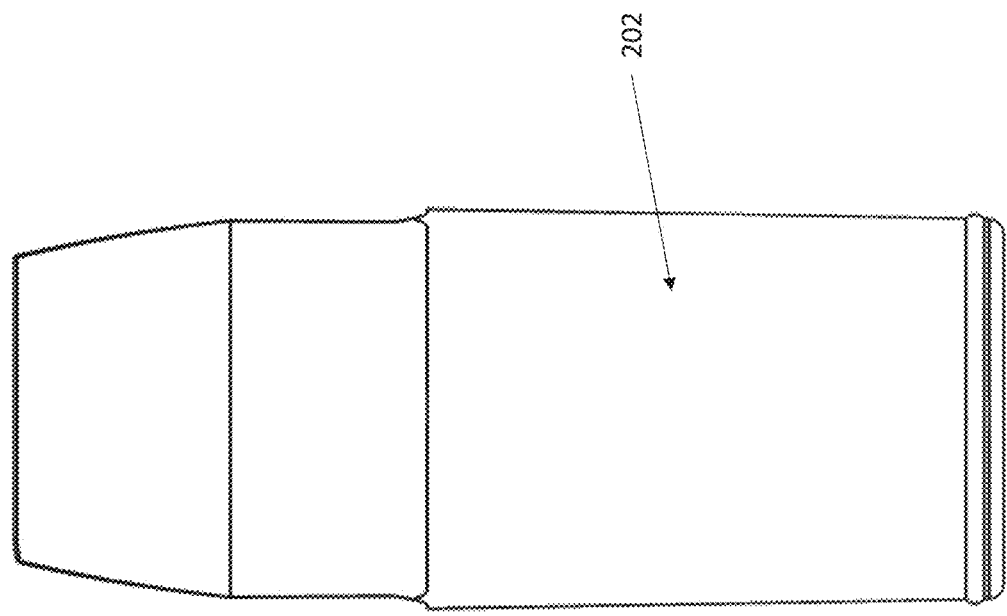
FIG. 4E is an exemplary front view illustration of a developer solution vial insert for use with an assay device, of the invention.
Figure 4F:
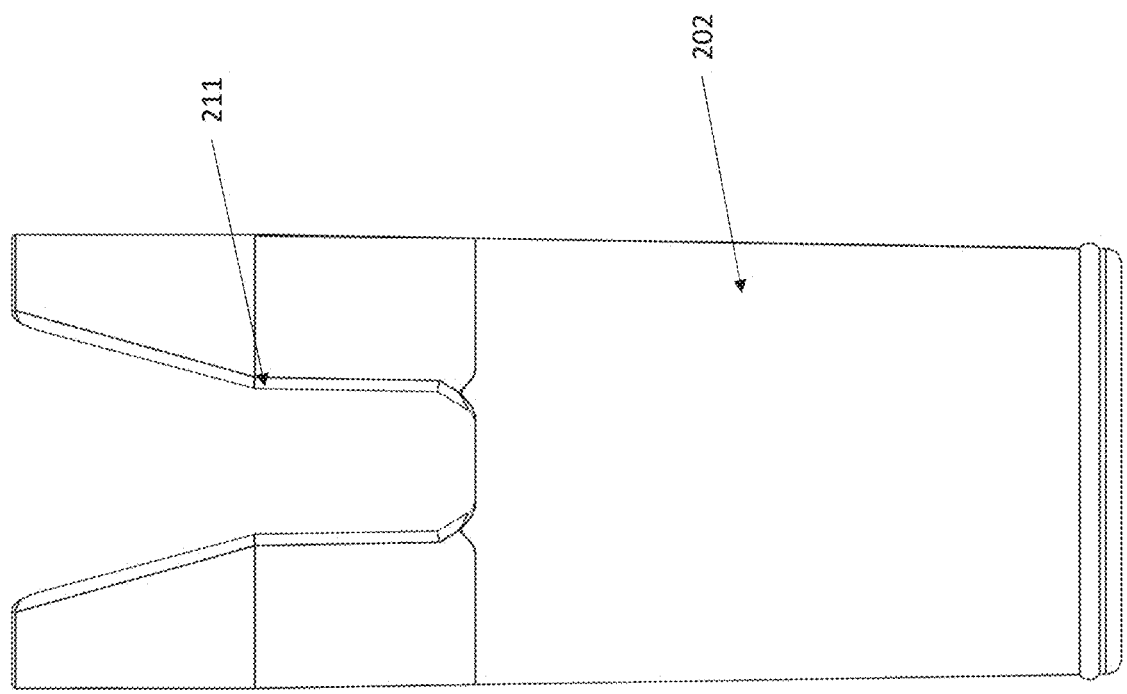
FIG. 4F is an exemplary side view illustration of a developer solution vial insert for use with an assay device, of the invention.

FIGS. 4E-4G show exemplary front, side, and side perspective view illustrations of a developer solution vial insert for use with an assay device, of the invention. As described in FIG. 4D above, the base 204 of the developer solution vial insert 200 may not be closed. Instead, the cavity 201 of the developer solution vial insert 200 may be capped by an corresponding container. For example, the developer solution vial insert 200 could mate with an elongated cylindrical housing, open on one end and closed on the bottom. The base 204 would be placed and sealed, even with the closed bottom of the cylindrical housing to contain the developer solution. The top of the elongated cylindrical housing would extend beyond the guiding wall portion 211 to prevent accidental spillage of developer solution in the combined developer solution vial insert 200 and elongated cylindrical housing.

Figure 4H:
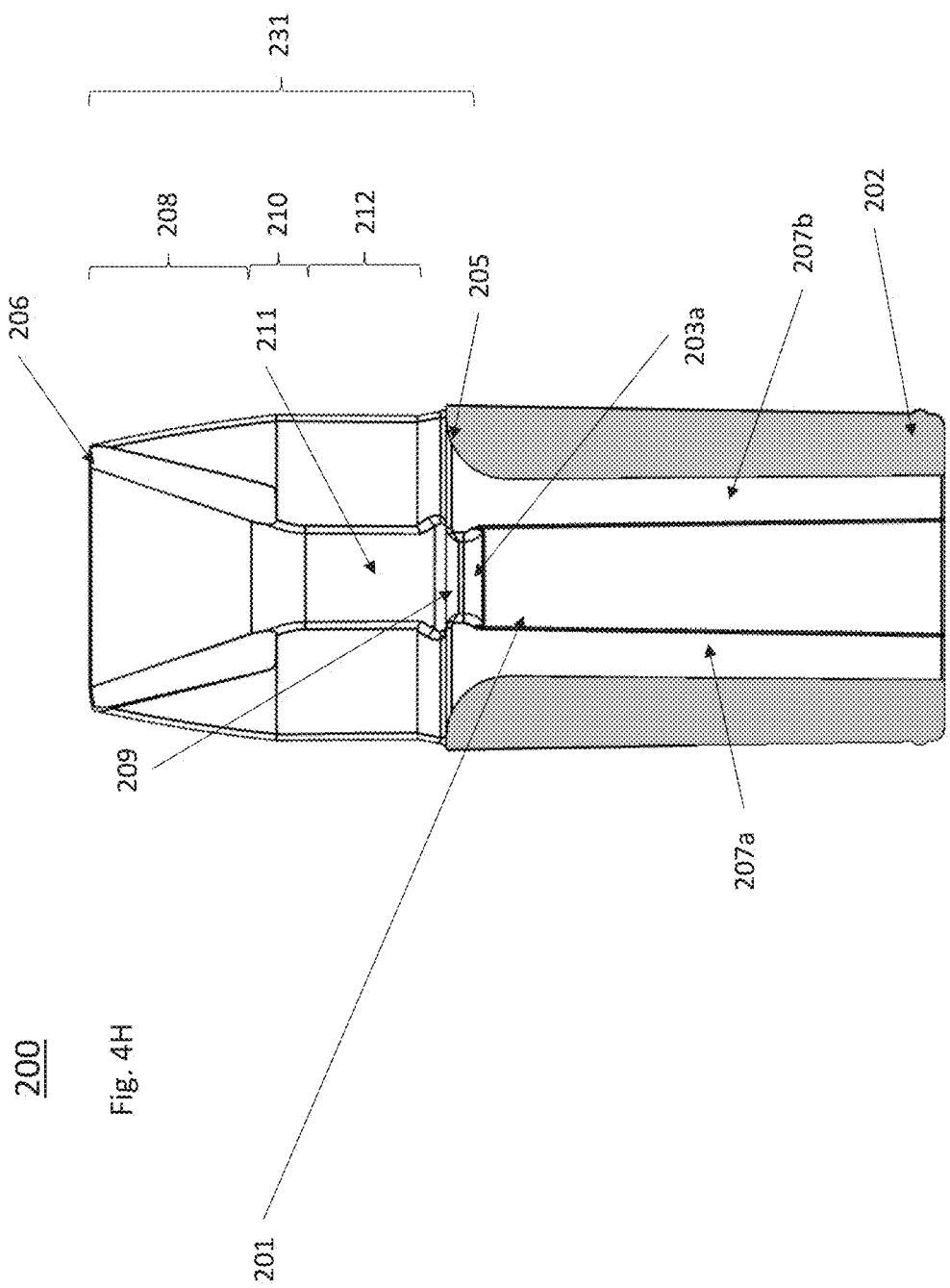
FIG. 4H is an exemplary cross-sectional front view illustration of a developer solution vial insert of FIGS. 4A-4G for use with an assay device from section D-D of one embodiment of the invention.

FIGS. 4H and 4I show exemplary cross-sectional front and front perspective view illustrations of the developer solution vial insert of FIGS. 4A-4G for use with an assay device from section D-D of one embodiment of the invention. Similar to the features in FIGS. 3A and 3B, the cross-sectional illustrations more clearly show the dimensions and shape of each portion of the developer solution vial insert 200. For example, the guiding wall portion 211 includes a first section 208, second section 210, and third section 212. Each section cross-sectionally narrows from the opening 206 of the developer solution vial insert 200 to the top of the seating portion 205.

Figure 5A:
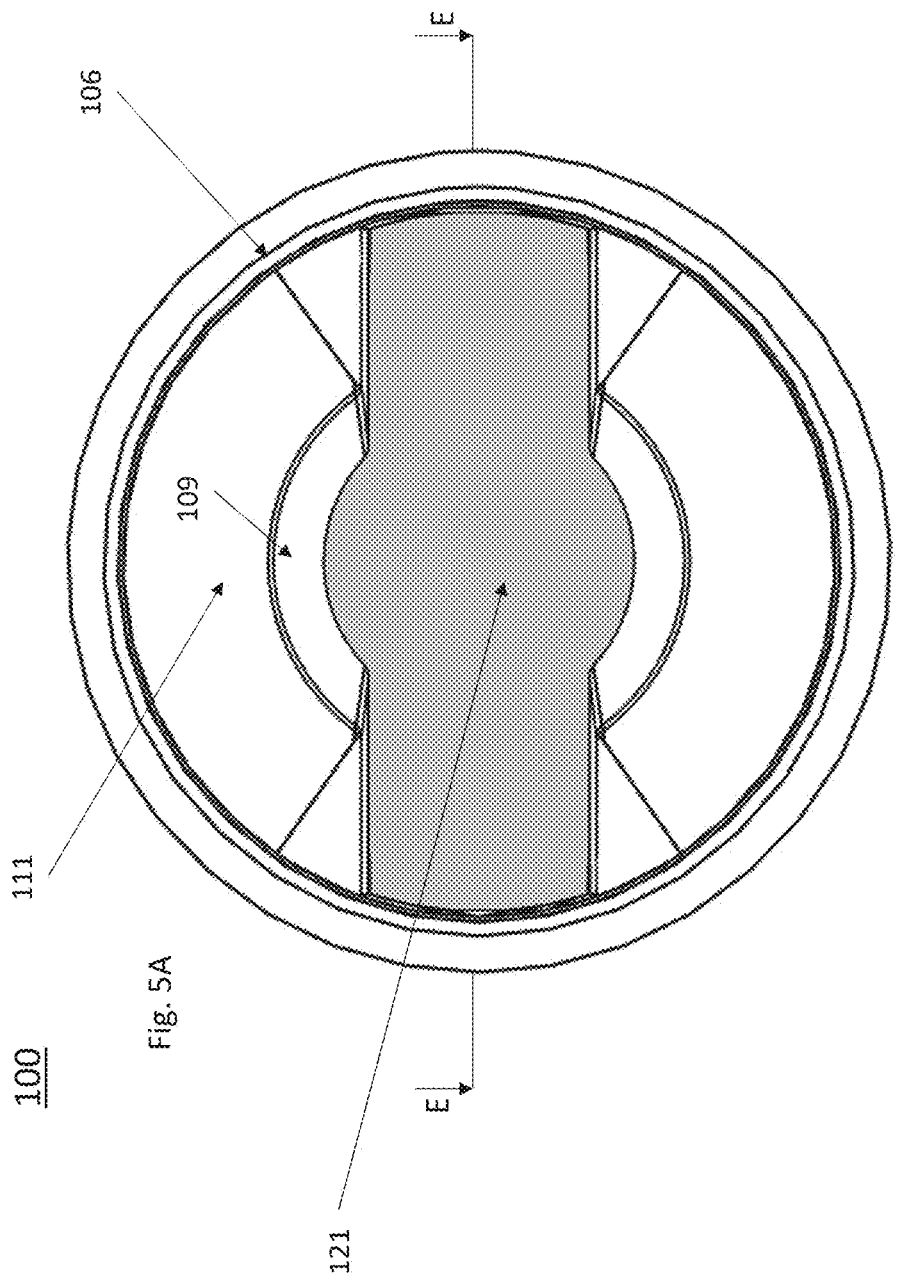
FIG. 5A is an exemplary top view illustration of a developer solution vial filled with developer solution for use with an assay device, of the invention.
Figure 5D:
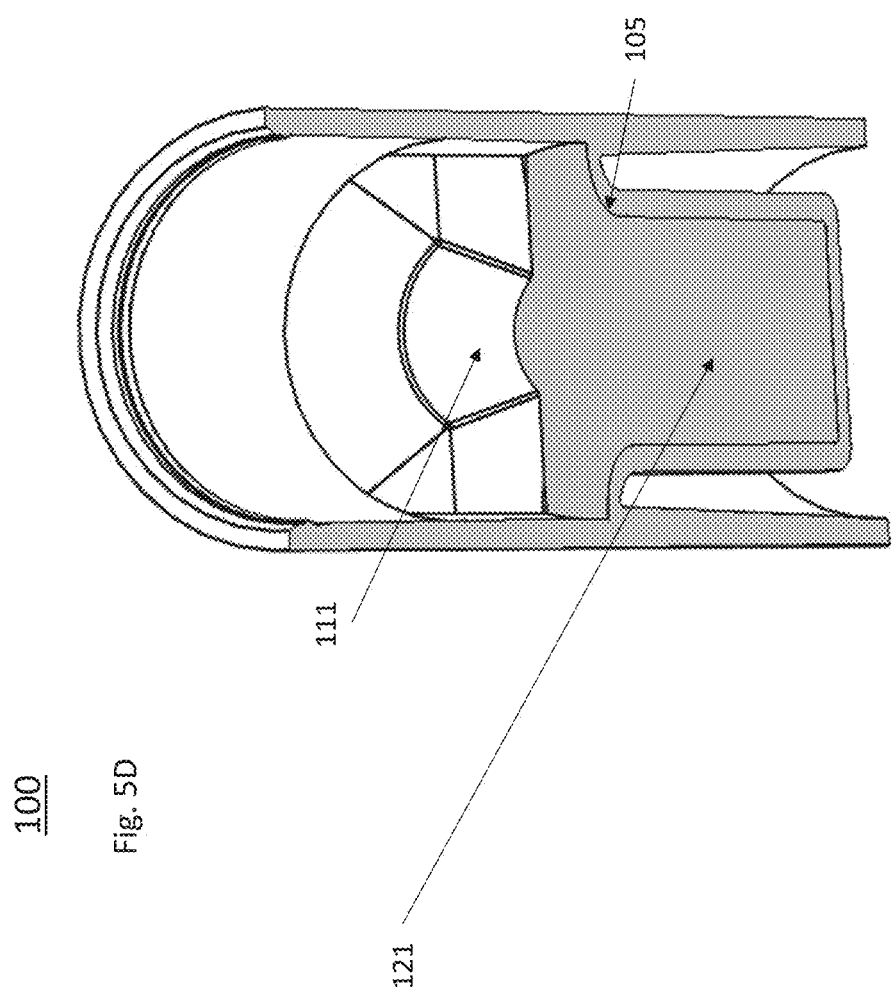
FIG. 5D is an exemplary cross-sectional front perspective view illustration of a developer solution vial for use with an assay device from section E-E of one embodiment of a developer solution vial of FIG. 5A of the invention.

FIGS. 5A and 5B show exemplary top and top perspective view illustrations of the developer solution vial of FIGS. 1A-3B for use with an assay device of one embodiment of the invention. FIGS. 5C and 5D show exemplary cross-sectional front and cross-sectional front perspective view illustrations of the developer solution vial of FIG. 5A for use with an assay device from section E-E of one embodiment of the invention. The developer solution vial 100 is filled with developer solution 121. As shown, the developer solution 121 is filled to submerge the extraction portion 103 and submerge the top edge of the seating portion 105 and sampling device interface portion 109. However, in some embodiments, the seating portion 105 remains above a fill-line and is not submerged in the developer solution. In some embodiments, the developer solution vial 100 includes a marked fill-line, in other embodiments, the developer solution vial 100 does not include a marking for the fill-line.

Figure 6E:
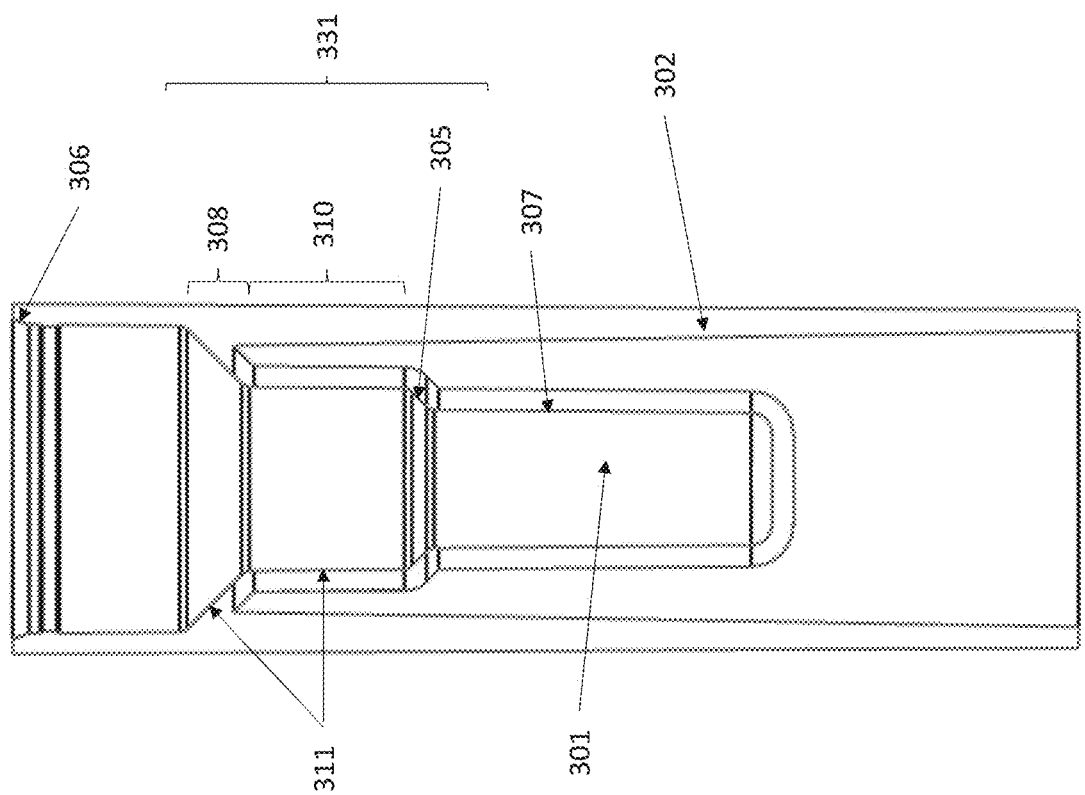
FIG. 6E is an exemplary cross-sectional front view illustration of a minimized developer solution vial of FIG. 6A for use with an assay device from section F-F of one embodiment of the invention.

FIGS. 6A and 6B show exemplary top and top perspective view illustrations of a minimized developer solution vial for use with an assay device of one embodiment of the invention. The minimized developer solution vial 300 includes a cavity 301 and elongated housing 302 with mating portion 331 (see, e.g., FIG. 6E) for interfacing with assay devices. The mating portion 331 including seating portion 305, sidewall portion 307, and guiding wall portion 311. The seating portion 305 is configured to mate with a shortened direct sampling device. The shortened direct sampling device includes a straight collection pad. The shortened direct sampling device with a housing that mates with the seating portion 305 to rest the shortened direct sampling device in the minimized developer solution vial 300 without resting collection pad of the shortened direct sampling device at the bottom of the minimized developer solution vial 300. The sidewall portion 307 is substantially longitudinally straight since the collection pad has a generally rectangular shape. The guiding wall portion 311 helps to guide the shortened direct sampling device toward the center of the minimized developer vial cavity 301.

FIGS. 6C and 6D show exemplary bottom and bottom perspective view illustrations of the minimized developer solution vial for use with an assay device of one embodiment of the invention. The base 304 of the minimized developer solution vial 300 helps to keep the minimized developer solution vial 300 upright while the shortened direct sampling device rests.

Figure 6F:
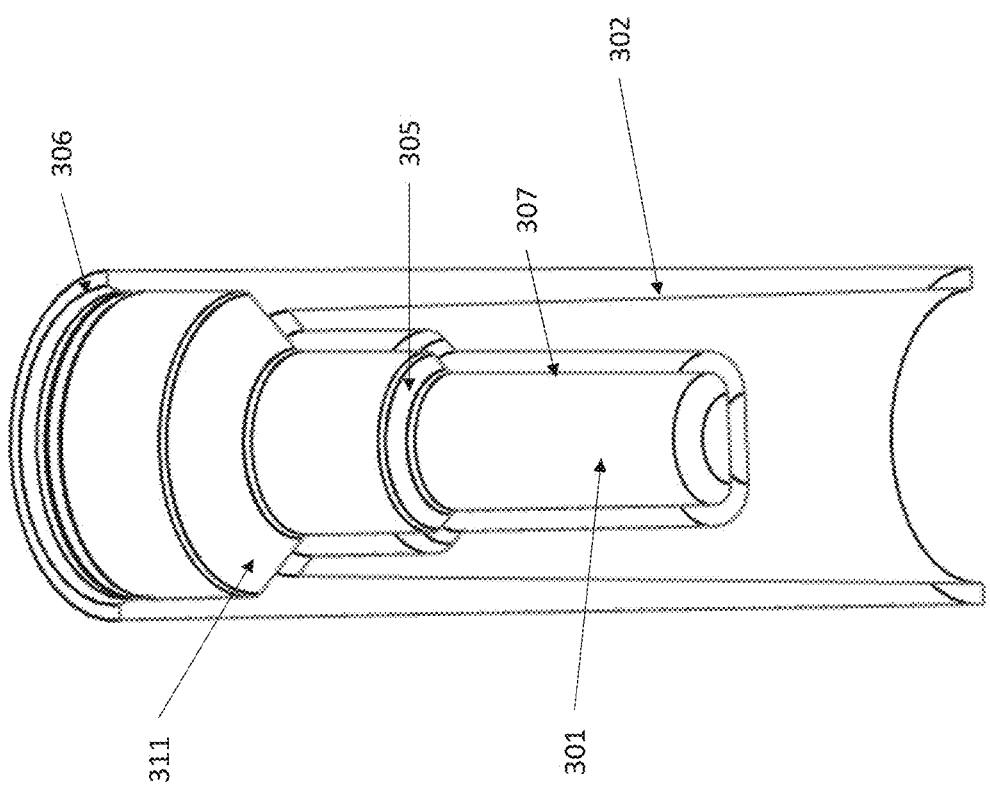
FIG. 6F is an exemplary cross-sectional front perspective view illustration of a minimized developer solution vial of FIG. 6A for use with an assay device from section F-F of one embodiment of the invention.

FIGS. 6E and 6F show exemplary cross-sectional front and front perspective view illustrations of the minimized developer solution vial of FIG. 6A for use with an assay device from section F-F of one embodiment of the invention. The guiding wall portion 311 includes an interior wall to the cavity that includes first section 308 and second section 310. The second section 310 surrounds a housing of the shortened direct sampling device mated to the seating portion 305. The first section 308 is between opening 306 and the top of the second section 310. As shown, the minimized developer solution vial 300 does not include an extraction portion and uses only an assay device that may also be used to directly collect a sample from a patient.

Figure 7A:
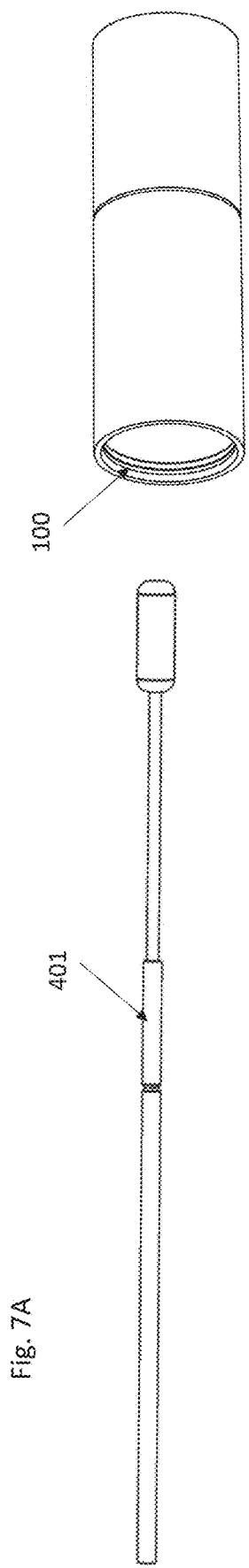
FIGS. 7A-D are exemplary front view illustrations of a swab in use with a developer solution vial, of the invention.
Figure 7B:
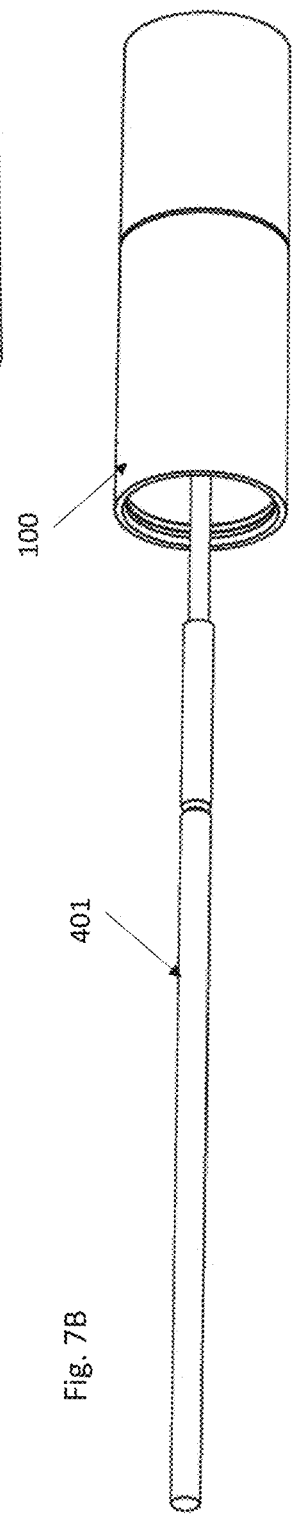
Figure 7C:
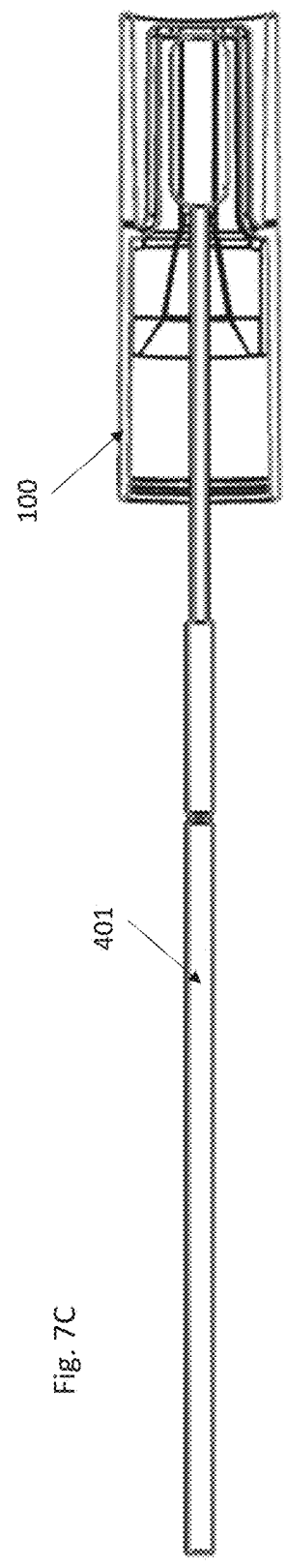
Figure 7D:
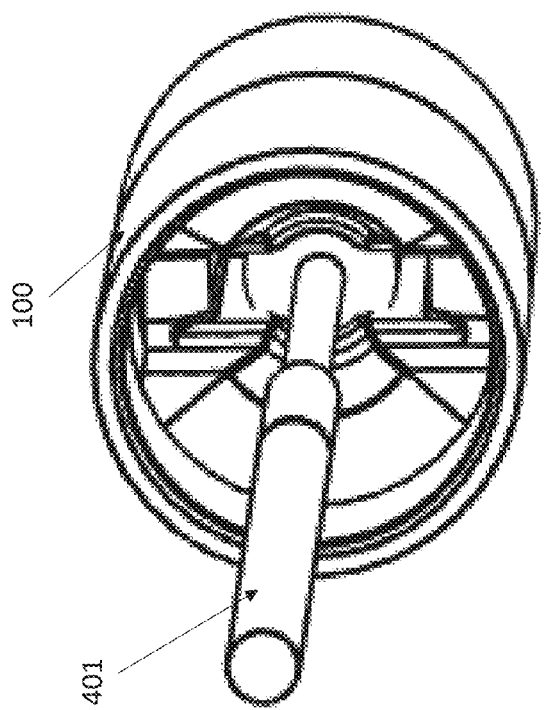

FIGS. 7A-D show exemplary front view illustrations of a swab in use with a developer solution vial of FIGS. 1A-3B, of the invention. The figures show a sampling device 401 that is a swab entering and interfacing with the developer solution vial 100. FIG. 7A shows the sampling device 401 and developer solution vial 100 separately. FIGS. 7B-7D shows the sampling device 401 in the developer solution vial 100 from various views. FIG. 7C shows a cross-sectional view of the mated sampling device 401 and developer solution vial 100, showing how the sampling device 401 would be centered and squeeze through the extraction portion into the developer solution vial cavity to elute a sample into the developer solution.

Figure 8A:
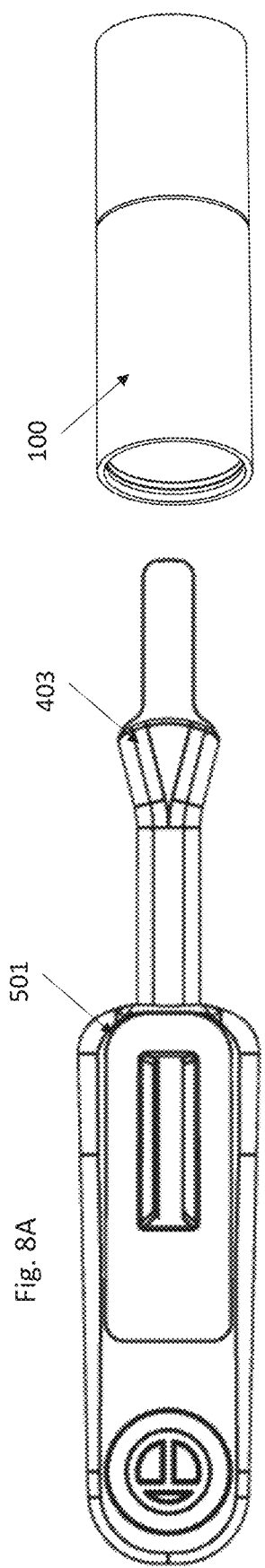
FIG. 8A-D are exemplary front view illustrations of a direct sample collection pad in use with a developer solution vial, of the invention.
Figure 8B:
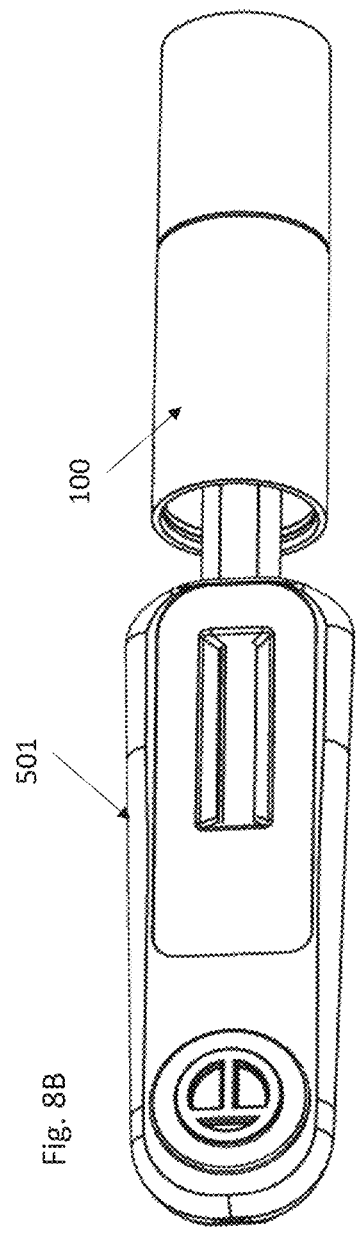
Figure 8C:
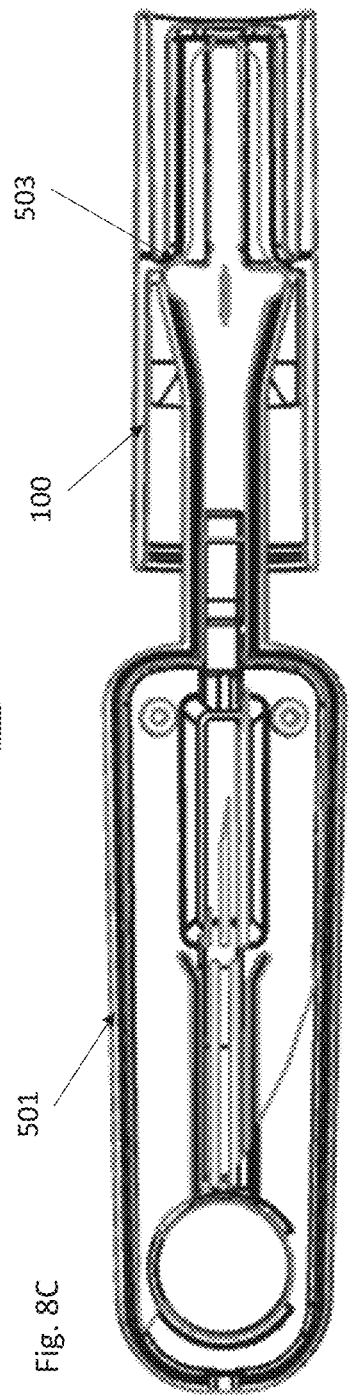
Figure 8D:
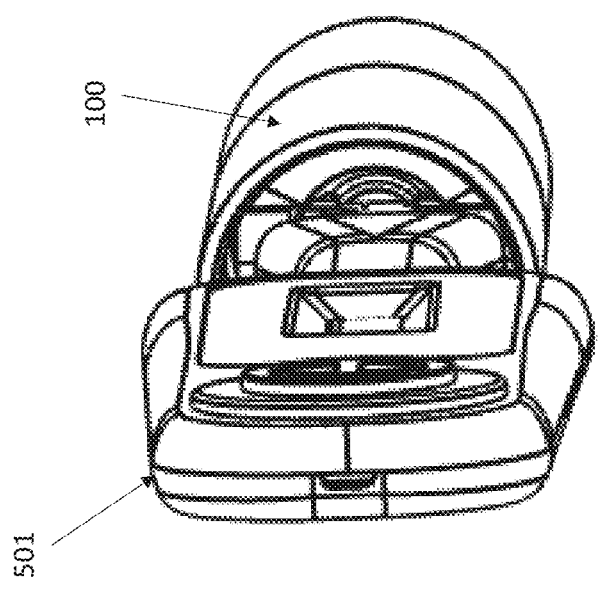

FIG. 8A-D show exemplary front view illustrations of an assay device with an integrated sampling device in use with a developer solution vial of FIGS. 1A-3B, of the invention. The figures show an assay device 501 with an integrated sampling device entering and interfacing with the developer solution vial 100. FIG. 8A shows the assay device 501 with an integrated sampling device and developer solution vial 100 separately. FIGS. 8B-8D shows the assay device 501 with an integrated sampling device in the developer solution vial 100 from various views. FIG. 8C shows a cross-sectional view of the mated assay device 501 with an integrated sampling device and developer solution vial 100, showing how the assay device 501 with an integrated sampling device would be centered and be seated at a seating surface 503 into the developer solution vial cavity to wick a sample from the developer solution into the assay device 501.

Figure 9D:
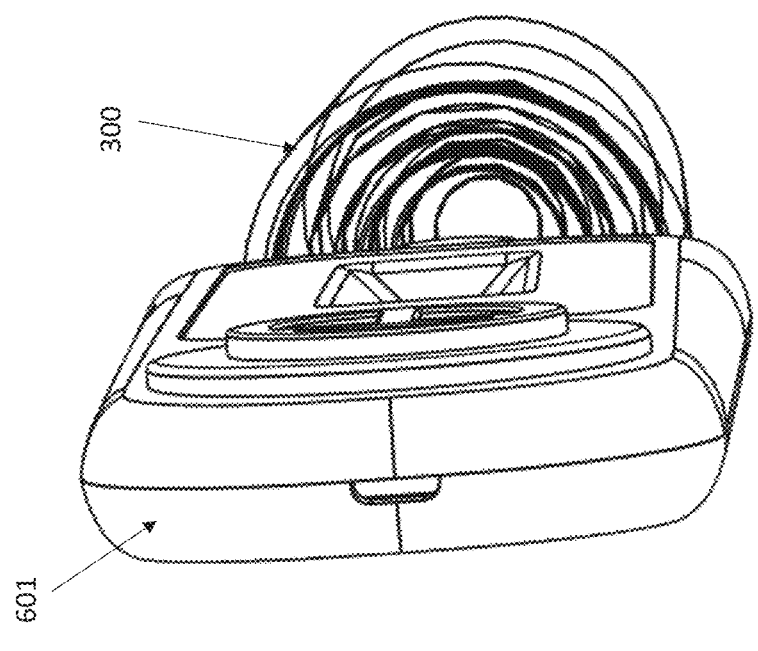

FIG. 9A-D show exemplary front view illustrations of a direct sample collection pad in use with the minimized developer solution vial of FIGS. 6A-6D, of the invention. The figures show a direct sampling and assay device 601 entering and interfacing with the developer solution vial 300. FIG. 9A shows the direct sampling and assay device 601 and developer solution 300 separately. FIGS. 9B-9D shows the direct sampling and assay device 601 in the developer solution vial 300 from various views. FIG. 9C shows a cross-sectional view of the direct sampling and assay device 601 and minimized developer solution vial 300, showing how the direct sampling and assay device 601 would be centered placed into the developer solution vial cavity to elute and wick a sample from the developer solution into the direct sampling and assay device 601.

Sampling and Testing

In a first embodiment, an assay method comprises the steps of collecting a sample on a sampling device. Inserting the sampling device with the collected sample in a developer solution vial keyed to a sampling device and assay device. Inserting the sampling device submerges the sampling device in developer solution held within a cavity of the developer solution vial to wet the sampling device with the developer solution. The sampling device is then agitated within the developer solution to elute the collected sample from the sampling device and mix the collected sample with the developer solution. Once agitated, the sampling device is removed from the developer solution. When removing the sampling device, an extraction portion of the developer solution vial further recovers some of the remaining developer solution and collected sample from the sampling device. Then an assay device is inserted into the developer solution to run the assay for diagnosis.

In a second embodiment, a second assay method comprises the steps of collecting a sample on a sampling device integrated with an assay device that directly collects samples. The sampling device of the assay device with the collected sample is inserted into a developer solution vial to submerge the sampling device of the assay device in the developer solution within the cavity of the developer solution vial to wet the sampling device with the developer solution and run the assay for the diagnosis.

In one embodiment, a method for using a developer solution vial with an assay device to diagnose a respiratory disease in a patient, of the invention. The method can be broken down into two main steps. The first step is collection, and the second step is testing.

In one embodiment, the collection steps begin with bringing the tests including both the developer solution vial and LFA to an operating temperature of 15°-40° C. (59°-104° F.). Setting up a testing stand for resting the developer solution vial. Another embodiment of the invention is a kit (not shown) where the LFA and developer solution vial come in a dual-chamber pouch which keeps the developer solution vial and LFA sanitary and prevents accidental adulteration of a test. The developer solution vial includes a cap which is gently rocked off the developer solution vial and seals the developer solution in the developer solution vial prior to use. The developer solution vial is placed into the slot in the stand.

The patient may then be instructed to blow their nose into a tissue and then discard. The patient removes the LFA device, such as assay device 501 above, from the pouch and checks for an absorbent packet which prevents absorption of liquid by the collection pad of an LFA. The collection pad should not be touched. The collection pad from the assay device is pressed firmly into a nostril against the nasal wall and rotated a number of times (15) in each nostril.

The testing steps begin by inserting the assay device into the developer solution vial on the testing stand. See FIGS. 9A-9C. The assay device may be agitated in the developer solution by swirling the collection pad of the assay device a number of times (10) and then leaving the assay device in the developer solution and returned to the testing stand. In other embodiments, the assay device or sampling device may be spun, tapped, or plunged up and down in the developer solution to elute the sample from the assay device 501 with the integrated sampling device, and into the developer solution. The user should make sure to leave a results window of the assay device facing the user. The user then leaves the assay device in the developer solution vial while the test is running for between 30 and 40 minutes. In one embodiment, a pink indicator fluid will appear and be wicked to the results window.

In some embodiments, the developer solution vial 100 may be shipped separate from the developer solution. Thus, the developer solution vial 100 may require filling. In some embodiments, the developer solution vial 100 may be made of a translucent, opaque, or transparent material that allows a user to see a mark for a fill-line and/or the amount of developer solution that has been added to the developer solution vial 100.

In some embodiments, the developer solution vial 100 uses an assay device that is configured to allow direct sample collection with an assay device 501 with an integrated sampling device. In such a case, agitation may not be necessary to elute the sample from the collection pad. Rather, simply inserting the assay device into the developer solution vial 100 may wick the sample directly into the through the assay strip of the assay device.

In some embodiments, a method includes at least the steps of collecting a sample with a sampling device; inserting the sampling device with the collected sample into a developer solution vial to a sufficient depth in a developer solution within the cavity to wet the sampling device with the developer solution; agitating the sampling device at a sufficient depth within the developer solution to elute the collected sample from the sampling device and mix the sample with the solution; withdrawing the sampling device from the developer solution vial such that the extraction portion of the developer solution vial to force a substantial portion of any sample or developer solution from the sampling device and into the cavity; and inserting a lateral flow assay device into the developer solution vial in the developer solution containing the sample to run the assay for diagnosis. In some embodiments, the sampling device may be wet with developer solution before collection of the sample from the patient.

Collecting the sample with a sampling device includes collection by a swab or applicator, or an assay device integrated with a sampling device, such as a collection pad that is capable of directly collecting samples. The sample may be collected from a patient or surface by pressing, swabbing, wiping, or dabbing at a bodily fluid of the patient or the surface. The collecting may require the user to wipe the surface or bodily fluid a number of times to better ensure collection of enough sample for the assay device to run the diagnostics. For example, wiping at the anterior nares five times to ensure good coverage by the sampling device.

The sampling device is then inserted into a developer solution vial 100 to submerge the sampling device in the developer solution within the cavity of the container to wet the sampling device with the solution and remove then remove the sample from the sampling device by elution. The elution may be through any number of methods from agitating the sampling device in the developer solution to pressing the sampling device against the extraction portion 103 to forcefully remove the sample from the sampling device. Agitating the sampling device at a depth within the developer solution to submerge the head of the sampling device and elute the collected sample from the sampling device and mix the sample with the developer solution may include swirling, rotating, shaking, tapping, push-pull motion, etc. The agitation should limit or prevent spillage of developer solution.

Once eluted, withdrawing the sampling device from the developer solution vial such that the extraction portion of the developer solution vial forces a substantial portion of any sample or developer solution from the sampling device and into the cavity. Then, inserting the assay device into the developer solution vial in the developer solution containing the sample to run the assay for diagnosis. The assay device may include any fluid flow assay devices, however is preferably a lateral flow assay device.

In the case of an assay device integrated with a sampling device, such as a collection pad that is configured to directly collect samples, the assay device collects the sample at the sampling device of the assay device. The sampling device is then inserted into the developer solution vial cavity with the developer solution to wet the sampling device and wick the sample into the rest of the assay device. The sample moves through the assay strip of the assay device and eventually displays the results for diagnosis.

Although the invention has been described with reference to various exemplary embodiments, it is to be understood that these embodiments are merely illustrative of the principles and applications of the invention. Those having skill in the art would recognize that various modifications to the exemplary embodiments may be made, without departing from the scope of the invention. Various features and/or characteristics of differing embodiments of the invention may be combined with one another. Any directional aspects of an enclosure device of the invention as it is described, oriented or appears in the drawings are presented for convenience only; they are not intended to be limiting or to imply that the device has to be used or positioned in any particular orientation.

The invention claimed is:

1. A developer solution vial for use with an assay device for a point-of-care diagnosis, comprising:
    a cavity to contain a developer solution; and
    an elongated housing surrounding the cavity and comprising an opening extending to the cavity, and a mating portion to interface with a head of a sampling device and/or a collection pad of the assay device, the mating portion comprising, in outward order from cavity opening:
        an extraction portion comprising a rounded semi-circular cross-sectional shape that protrudes into the cavity;
        a sampling device interface portion to accept the sampling device into the cavity to elute a sample into the developer solution, and
        a seating portion to mate with a resting surface of the collection pad of the assay device or housing of the collection pad of the assay device to prevent compression of a sampling portion of the collection pad when in a resting position in the developer solution.

2. The developer solution vial of claim 1, wherein the extraction portion promotes recovery of sample from the sampling device into the developer solution.

3. The developer solution vial of claim 2, wherein the extraction portion extends between two sides of the seating portion.

4. The developer solution vial of claim 3, wherein the extraction portion extends along both sides of the sampling device interface portion.

5. The developer solution vial of claim 2, wherein the extraction portion bottlenecks the sampling device interface portion to evenly receive sides of the head based on a width of the sampling device.

6. The developer solution vial of claim 2, wherein the extraction portion provides a compression and/or friction force to recover the developer solution and/or the sample remaining in the sampling device.

7. The developer solution vial of claim 1, wherein the cavity volume is between 75 and 1500 microliters (µL).

8. The developer solution vial of claim 1, wherein the cross-sectional shape of the mating portion is keyed to fit the sampling device and the assay device.

9. The developer solution vial of claim 1, wherein the developer solution vial comprises a transparent material.

10. The developer solution vial of claim 1, wherein the sampling device is a swab.

11. The developer solution vial of claim 1, wherein the developer solution vial includes a vial or an insert for a mated container.

12. The developer solution vial of claim 1, further comprising between 50 and 1000 microliters of a developer solution in the cavity.

13. An assay method comprising the steps of:
collecting a sample on a sampling device,
inserting the sampling device with the collected sample in the developer solution vial of claim 12, comprising the extraction portion in the sampling device interface portion to promote recovery of the sample from the sampling device into the developer solution, to submerge the sampling device in developer solution within the cavity to wet the sampling device with the developer solution,
agitating the sampling device within the developer solution to elute the collected sample from the sampling device and mix the collected sample with the developer solution,
withdrawing the sampling device from the developer solution vial so the extraction portion of the developer solution vial recovers a portion of any of the collected sample and/or the developer solution remaining on the agitated sampling device into the cavity, and
inserting the assay device into the developer solution vial in the developer solution containing the collected sample to run the assay for the diagnosis.

14. The method of claim 13, further comprising:
waiting a predetermined testing time while the assay device is seated in the developer solution vial.

15. The method of claim 13, wherein the developer solution vial is kept in an upright position during the assay.

16. An assay method comprising the steps of:
collecting a sample on a sampling device integrated with an assay device; and
inserting the sampling device of the assay device with the collected sample in the developer solution vial of claim 12 to submerge the sampling device in the developer solution within the cavity to wet the sampling device with the developer solution to run the assay for the diagnosis.

17. The method of claim 16, further comprising the step of:
agitating the sampling device within the developer solution to elute the collected sample from the sampling device and mix the collected sample with the developer solution.

18. The method of claim 16, further comprising the step of:
waiting a predetermined testing time while the assay device is seated in the developer solution vial.

19. The method of claim 16, wherein the developer solution vial is kept in an upright position during the assay.

* * * * *